(12) United States Patent
Tachi et al.

(10) Patent No.: US 9,012,356 B2
(45) Date of Patent: Apr. 21, 2015

(54) METHOD FOR PRODUCING POLYACRYLIC ACID (SALT)-BASED WATER ABSORBENT RESIN

(71) Applicant: Nippon Shokubai Co., Ltd., Osaka (JP)

(72) Inventors: Koji Tachi, Himeji (JP); Hironori Sato, Himeji (JP); Kazushi Torii, Himeji (JP); Hiroyuki Ikeuchi, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 14/358,638

(22) PCT Filed: Nov. 16, 2012

(86) PCT No.: PCT/JP2012/079836
§ 371 (c)(1),
(2) Date: May 15, 2014

(87) PCT Pub. No.: WO2013/073682
PCT Pub. Date: May 23, 2013

(65) Prior Publication Data
US 2014/0371400 A1 Dec. 18, 2014

(30) Foreign Application Priority Data
Nov. 16, 2011 (JP) .................... 2011-251103

(51) Int. Cl.
| C08L 33/02 | (2006.01) |
| C08J 3/24 | (2006.01) |
| C08F 20/06 | (2006.01) |
| A61L 15/24 | (2006.01) |
| A61L 15/60 | (2006.01) |
| C08F 220/06 | (2006.01) |
| C08F 120/06 | (2006.01) |

(52) U.S. Cl.
CPC ............... *C08J 3/245* (2013.01); *C08L 33/02* (2013.01); *C08F 20/06* (2013.01); *A61L 15/24* (2013.01); *A61L 15/60* (2013.01); *C08F 220/06* (2013.01); *C08F 120/06* (2013.01); *C08J 2333/02* (2013.01)

(58) Field of Classification Search
None
See application file for complete search history.

(56) References Cited

U.S. PATENT DOCUMENTS

| 5,124,416 | A | * | 6/1992 | Haruna et al. ................. 526/62 |
| 5,380,808 | A |  | 1/1995 | Sumiya et al. |
| 5,478,879 | A |  | 12/1995 | Kajikawa et al. |
| 5,562,646 | A |  | 10/1996 | Goldman et al. |
| 6,164,455 | A |  | 12/2000 | Kakita et al. |
| 6,228,930 | B1 |  | 5/2001 | Dairoku et al. |
| 6,241,928 | B1 |  | 6/2001 | Hatsuda et al. |
| 6,562,879 | B1 |  | 5/2003 | Hatsuda et al. |
| 6,710,141 | B1 | * | 3/2004 | Heide et al. ..................... 526/88 |
| 6,867,269 | B2 |  | 3/2005 | Sakamoto et al. |
| 6,906,159 | B2 |  | 6/2005 | Dairoku et al. |
| 6,987,151 | B2 |  | 1/2006 | Gartner et al. |
| 7,169,843 | B2 |  | 1/2007 | Smith et al. |
| 7,173,086 | B2 |  | 2/2007 | Smith et al. |
| 7,265,190 | B2 |  | 9/2007 | Dairoku et al. |
| 7,622,535 | B2 |  | 11/2009 | Dairoku et al. |
| 7,638,078 | B2 |  | 12/2009 | Sasabe et al. |
| 7,694,900 | B2 |  | 4/2010 | Irie et al. |
| 2002/0128618 | A1 |  | 9/2002 | Frenz et al. |
| 2004/0110897 | A1 |  | 6/2004 | Sakamoto et al. |
| 2005/0046069 | A1 |  | 3/2005 | Sasabe et al. |
| 2005/0215734 | A1 |  | 9/2005 | Dairoku et al. |
| 2005/0245684 | A1 |  | 11/2005 | Daniel et al. |

(Continued)

FOREIGN PATENT DOCUMENTS

| EP | 0496067 | 12/1991 |
| JP | 55-108407 | 8/1980 |

(Continued)

OTHER PUBLICATIONS

Modern Superabsorbent Polymer Technology (1998), pp. 69-103.

(Continued)

*Primary Examiner* — Robert C Boyle
(74) *Attorney, Agent, or Firm* — Roylance, Abrams, Berdo & Goodman, L.L.P.

(57) ABSTRACT

The purpose of the present invention is to provide a method for producing a water absorbent resin having improved physical properties, particularly, improved saline flow conductivity (SFC) and less amount of fine powder. The present invention provides a method for producing a polyacrylic acid (salt)-based water absorbent resin, the method comprising: a polymerization step of supplying as a base material an aqueous solution containing an acrylic acid and/or an acrylic acid salt as a monomer component and polymerizing the monomer in the presence of a polymerization initiator, wherein in the polymerization step, there is used a polymerization apparatus which comprises a polymerization part covered with a case, said polymerization part comprising at least a supply line for supplying the aqueous solution, an external gas supply port, and a gas discharge port, and has a structure that a liquid contact part in contact with the aqueous solution and a gas supplied from the outside of the polymerization apparatus are brought into contact with the aqueous solution during a polymerization, and assuming that a controlled temperature of the liquid contact part is set as TS, a temperature of the gas part is set as TG, and TT is (TS+TG)/2, the polymerization is carried out under temperature conditions satisfying the following Equations 1 to 3:

$$35°\text{ C.} \leq TS \leq 85°\text{ C.},\qquad \text{Equation 1:}$$

$$40°\text{ C.} \leq TG \leq 90°\text{ C.},\qquad \text{Equation 2:}$$

$$47°\text{ C.} \leq TT \leq 73°\text{ C.}\qquad \text{Equation 3:}$$

17 Claims, 3 Drawing Sheets

(56) References Cited

U.S. PATENT DOCUMENTS

| | | |
|---|---|---|
| 2005/0256469 A1 | 11/2005 | Qin et al. |
| 2006/0167198 A1 | 7/2006 | Sasabe et al. |
| 2007/0293617 A1 | 12/2007 | Riegel et al. |
| 2008/0004408 A1 | 1/2008 | Stueven et al. |
| 2008/0080300 A1 | 4/2008 | Stueven et al. |
| 2008/0114129 A1 | 5/2008 | Herfert et al. |
| 2008/0202987 A1* | 8/2008 | Weismantel et al. ........... 209/32 |
| 2008/0221237 A1 | 9/2008 | Herfert et al. |
| 2009/0194462 A1 | 8/2009 | Stueven et al. |
| 2009/0204087 A1 | 8/2009 | Herfert et al. |
| 2009/0261023 A1 | 10/2009 | Stueven et al. |
| 2009/0266747 A1 | 10/2009 | Stueven et al. |
| 2010/0010461 A1 | 1/2010 | Herfert et al. |
| 2010/0041550 A1 | 2/2010 | Riegel et al. |
| 2010/0041824 A1 | 2/2010 | Torii et al. |
| 2010/0042612 A1 | 2/2010 | Gomaa |
| 2010/0063469 A1 | 3/2010 | Herfert |
| 2011/0015362 A1 | 1/2011 | Weismantel et al. |
| 2011/0021725 A1 | 1/2011 | Takaai et al. |
| 2011/0059329 A1* | 3/2011 | Dobrawa et al. .............. 428/522 |
| 2011/0166300 A1* | 7/2011 | Dairoku et al. ................ 525/384 |
| 2012/0258851 A1 | 10/2012 | Nakatsuru et al. |

FOREIGN PATENT DOCUMENTS

| | | |
|---|---|---|
| JP | 2003-261601 | 9/2003 |
| JP | 2005-096448 | 4/2005 |
| JP | 2005-307195 | 11/2005 |
| JP | 2006-160866 | 6/2006 |
| JP | 2010-521538 | 6/2010 |
| WO | 2009/123197 | 10/2009 |
| WO | 2011/078298 | 6/2011 |

OTHER PUBLICATIONS

International Search Report for PCT/JP2012/079836, dated Jan. 22, 2013.
International Preliminary Report on Patentability for PCT/JP2012/079836, dated May 30, 2014, and English Translation thereof.

* cited by examiner

[Chemical Formula 2]

METHOD FOR PRODUCING POLYACRYLIC ACID (SALT)-BASED WATER ABSORBENT RESIN

FIELD OF THE INVENTION

The present invention relates to a method for producing a water absorbent resin. More specifically, it relates to a method for producing a water absorbent resin having a small load for fine powder recycling because of a small amount of fine powder generated after drying and pulverization and having improved physical properties (particularly, liquid permeability, typically, saline flow conductivity (SFC)).

DESCRIPTION OF THE RELATED ART

A water absorbent resin (SAP/Super Absorbent Polymer) is a polymer gelling agent having water-swelling ability and water-insolubility and has been widely used generally in a powdery form of 1 mm or less for disposable application, for example, absorbent articles such as a disposable diaper and a sanitary napkin, and an agricultural and horticultural water retaining agent, an industrial water cutoff material, and the like. For such a water absorbent resin, many monomers and hydrophilic polymers have been proposed as a raw material. Particularly, a polyacrylic acid (salt)-based absorbent resin using an acrylic acid and/or a salt thereof as a monomer has high absorbent performance, and thus is being mostly used industrially.

Such a water absorbent resin is produced through a polymerization step, a drying step, an optional step for removing non-dried products, a pulverization step, a classification step, a surface cross-linking step, and the like (Non-Patent Literature 1). With the high performance conversion technology of a disposable diaper that is a major use of the water absorbent resin, many functions (physical properties) are required of the water absorbent resin.

As a conventional method for producing a water absorbent resin, there are known methods, for example, a method for controlling a temperature difference between a temperature in polymerization system during polymerization gelation reaction and a gas temperature of a vapor-phase part in the polymerization system within a constant range (Patent Literature 1), a method for insulation-polymerizing an aqueous hydrophilic vinyl-based monomer solution in a specific container (Patent Literature 2), and a method for producing a water absorbent resin using an apparatus for continuous producing a water absorbent resin which comprises a movable endless revolving support belt, a monomer mixture supplying device, and a device for discharging a shaped hydrogel of absorbent resin, and is provided near each of opposite lateral parts of said movable endless revolving support belt with a lateral weir adapted to move in concert with said belt (Patent Literature 3). A constant temperature polymerization (Patent Literatures 4 and 5) for controlling a temperature change during polymerization has been also known. In addition, there are also known methods such as a technique for performing polymerization in a state of boiling at 100° C. or higher or a technique for initiating polymerization at a high temperature such as 40° C. or higher (Patent Literatures 6 to 8 and 36 to 41). Polymerization by a continuous kneader has been also known (Patent Literatures 42 to 45).

However, those methods are insufficient to satisfy the performances required for the latest higher degree water absorbent resin. To be specific, physical properties not simply limited to high water absorption capacity but also including gel strength, water soluble component, water absorption rate, water absorption capacity under load, liquid permeability, particle size distribution, urine resistance, antibacterial properties, impact resistance (damage resistance), powder fluidity, deodorant property, coloration resistance (degree of whiteness), low dust property, and the like, are required for the water absorbent resin. Therefore, numerous suggestions have been made such as surface cross-linking technique, additives, modification of production step, and the like.

Among the physical properties described above, due to increased amount of water absorbent resin used in a disposable diaper (for example, 50 wt % or more), liquid permeability has been regarded as a more important factor in recent years. Furthermore, there have been suggested many methods or techniques for improving liquid permeability under load or liquid permeability without load, such as SFC (Saline Flow Conductivity; Patent Literature 9) and GBP (Gel Bed Permeability; Patent Literatures 10 to 12).

As a method for improving liquid permeability, surface cross-linking or particle size control (reduced amount of fine powder) has been suggested in Patent Literature 9 and the like. However, since water absorption capacity (CRC) is generally counter to liquid permeability (for example, GBP/SFC), improvement in liquid permeability sacrifices water absorption capacity (CRC). Therefore, specifically, as a method for improving liquid permeability such as SFC or GBP, in addition to Patent Literatures 9 to 12, there have been known a technique for adding plaster before or during polymerization (Patent Literature 13), a technique for adding a spacer (Patent Literature 14), a technique for using a nitrogen-containing polymer having 5-17 mol/kg nitrogen atom capable of being protonated (Patent Literature 15), a technique for using polyamine and polyvalent metal ions or polyvalent anions (Patent Literature 16), a technique for covering, with polyamine, a water absorbent resin having a pH of less than 6 (Patent Literature 17), and a technique for using polyammonium carbonate (Patent Literature 18). In addition, there have been known a technique for using polyamine having a water soluble component of not less than 3%, and a technique for defining wicking index (WI) and gel integrity (Patent Literatures 19 to 21). There have been also known techniques for using polyvalent metal salt while controlling amount of methoxyphenol that is a polymerization inhibitor in polymerization, in order to improve coloring and liquid permeability (Patent Literatures 22 and 23). Moreover, there has been known a technique for polishing particles so as to attain high bulk specific gravity (Patent Literature 24).

However, although many methods for improving liquid permeability have been suggested as described above, there have been many problems that an effect of the improvement is insufficient, other physical properties, such as water absorption capacity (CRC), water absorption rate (for example, Vortex/FSR), or suction property (for example, FHA/CSF) have been sacrificed, the methods are disadvantageous in terms of cost, or processes are complicated, and stable production cannot be achieved.

Further, in addition to the above-described problems on physical properties (particularly, liquid permeability), problems of fine powder and recycling thereof also have been problematic.

That is, in a water absorbent resin obtained by polymerization and drying, fine powder (particularly, powder that passes through a standard sieve of 150 μm) is contained in an amount of 10 wt % to 40 wt % in obtained powder with a diameter of 1 mm or less. Such fine powder undesirably causes dust, caking at high humidity, and gel blocking in a diaper. Therefore, the fine powder in the water absorbent resin is removed by classification, and it may be discarded or recycled in the manufacturing process as necessary (Patent Literatures 25 to 35). Methods of recycling fine powder such as recycling with monomers (Patent Literature 25), recycling to polymerized gel (Patent Literatures 26 to 28), recycling after agglomeration have been known (Patent Literature 29). Further, there have been suggested methods for classifying a water absorbent resin to efficiently remove fine powder (Patent Literatures 30 to 35).

However, removal of fine powders by classification causes not only increase in cost of classification system but also decrease in yield of a water absorbent resin. Further, an increased amount of recycled fine powder for removing fine powder causes not only increase in manufacturing costs but also decrease in productivity, and in some cases, it may cause deterioration in physical properties due to recycling of fine powder.

Further, the present inventors have proposed various methods in Patent Literatures 1 to 8 and Patent Literatures 36 to 45 as a method for polymerizing a water absorbent resin. Among these methods, according to the techniques (Patent Literatures 6 to 8, Patent Literatures 36 to 41) of performing polymerization in a boiling state or initiating polymerization at a high temperature, it is possible to produce a water absorbent resin with high physical properties through polymerization in a short time (for example, within 10 minutes).

CITATION LIST

Patent Literature

Patent Literature 1: JP 2006-160866 A
Patent Literature 2: JP 55-108407 A
Patent Literature 3: U.S. Pat. No. 6,241,928 A
Patent Literature 4: U.S. Pat. No. 5,380,808
Patent Literature 5: EP 0496067 A
Patent Literature 6: U.S. Pat. No. 7,265,190
Patent Literature 7: U.S. Pat. No. 6,906,159
Patent Literature 8: U.S. Pat. No. 6,867,269
Patent Literature 9: U.S. Pat. No. 5,562,646
Patent Literature 10: US 2005/0,256,469 A
Patent Literature 11: U.S. Pat. No. 7,169,843
Patent Literature 12: U.S. Pat. No. 7,173,086
Patent Literature 13: US 2007/0,293,617 A
Patent Literature 14: US 2002/0,128,618 A
Patent Literature 15: US 2005/0,245,684 A
Patent Literature 16: US 2008/0,221,237 A
Patent Literature 17: US 2008/0,202,987 A
Patent Literature 18: US 2008/0,114,129 A
Patent Literature 19: US 2010/0,063,469 A
Patent Literature 20: US 2009/0,204,087 A
Patent Literature 21: US 2010/0,010,461 A
Patent Literature 22: US 2010/0,041,550 A
Patent Literature 23: US 2010/0,042,612 A
Patent Literature 24: U.S. Pat. No. 6,562,879
Patent Literature 25: U.S. Pat. No. 5,478,879
Patent Literature 26: U.S. Pat. No. 5,478,879
Patent Literature 27: U.S. Pat. No. 6,987,151
Patent Literature 28: US 2008/0,080,300 A
Patent Literature 29: U.S. Pat. No. 6,228,930
Patent Literature 30: U.S. Pat. No. 6,164,455
Patent Literature 31: US 2008/0,202,987 A
Patent Literature 32: US 2009/0,261,023 A
Patent Literature 33: US 2009/0,194,462 A
Patent Literature 34: US 2009/0,266,747 A
Patent Literature 35: US 2011/0,166,300 A
Patent Literature 36: US 2011/0,021,725 A
Patent Literature 37: U.S. Pat. No. 7,622,535
Patent Literature 38: US 2006/0,167,198 A
Patent Literature 39: U.S. Pat. No. 7,694,900
Patent Literature 40: U.S. Pat. No. 7,638,078
Patent Literature 41: US 2011/0,021,725 A
Patent Literature 42: U.S. Pat. No. 6,710,141
Patent Literature 43: U.S. Pat. No. 6,987,151
Patent Literature 44: US 2008/0,004,408 A
Patent Literature 45: US 2011/0,015,362 A Non-Patent Literature Non-Patent Literature 1: Modern Superabsorbent Polymer Technology (1998), p 69-103

SUMMARY OF INVENTION

Problems to be Solved by the Present Invention

However, it was found that according to these methods, a large amount of fine powders may be generated in some cases.

Accordingly, an object of the present invention is to reduce a generation amount of fine powders after drying and pulverization. Further, another object of the present invention is to provide a method for producing a water absorbent resin having excellent physical properties, particularly, liquid permeability, or saline flow conductivity (SFC).

Means to Solve the Problem

The present inventors have conventionally proposed, in order to reduce fine powder, classification methods disclosed in the Patent Literatures 30 to 35 or methods for recycling fine powder disclosed in the Patent Literatures 25 to 29, and also proposed, in order to improve physical properties of a water absorbent resin (particularly, to improve liquid permeability), various methods disclosed in the Patent Literatures 1 to 24. Further, as a method for polymerizing a water absorbent resin, various methods disclosed in the Patent Literatures 1 to 8 and Patent Literatures 36 to 45 have been proposed. The present inventors have made diligent study in order to solve the problems, i.e., to reduce fine powder and improve liquid permeability, to find that it is important not to individually control but to correlatively control an immediately early temperature in polymerization, that is, "a temperature of a container" and "a temperature of gas" in contact with an aqueous polymerization solution in polymerization, which have not been conceived to solve the above-described problems.

Specifically, there is provided a method for producing a polyacrylic acid (salt)-based water absorbent resin, the method comprising a polymerization step of supplying as a base material an aqueous solution containing an acrylic acid and/or an acrylic acid salt as a monomer component and polymerizing the monomer in the presence of a polymerization initiator, wherein in the polymerization step, there is used a polymerization apparatus which comprises a polymerization part covered with a case, said polymerization part comprising at least a supply line for supplying the aqueous solution, an external gas supply port, and a gas discharge port, and has a structure that a liquid contact part in contact with the aqueous solution and a gas supplied from the outside of the polymerization apparatus are brought into contact with the aqueous solution during a polymerization, and assuming that a controlled temperature of the liquid contact part is set as TS (Temperatuer of Surface), a temperature of the gas part is set as TG (Temperatuer of Gas), and TT (Temperatuer of Total) is (TS+TG)/2, the polymerization is carried out under temperature conditions satisfying all the equations 1 to 3 as below.

$$35°\text{C} \leq TS \leq 85°\text{C} \qquad \text{Equation 1}$$

$$40°\text{C} \leq TG \leq 90°\text{C} \qquad \text{Equation 2}$$

$$47°\text{C} \leq TT \leq 73°\text{C} \qquad \text{Equation 3}$$

Effects of the Invention

According to the present invention, it is possible to reduce a generation amount of fine powders after drying and pulverization. Further, a polyacrylic acid (salt)-based water absorbent resin obtained by the method of the present invention has excellent absorption properties, particularly, liquid permeability or saline flow conductivity (SFC).

BRIEF DESCRIPTION OF THE DRAWINGS

The following is a brief description of the drawings in which.

DESCRIPTION OF EMBODIMENTS

The present invention relates to a method for producing a polyacrylic acid (salt)-based water absorbent resin, the method comprising a polymerization step of supplying as a base material an aqueous solution containing an acrylic acid and/or an acrylic acid salt as a monomer component and polymerizing the monomer in the presence of a polymerization initiator, wherein in the polymerization step, there is used a polymerization apparatus which comprises a polymerization part covered with a case, said polymerization part comprising at least a supply line for supplying the aqueous solution, an external gas supply port, and a gas discharge port, and has a structure that a liquid contact part in contact with the aqueous solution and a gas supplied from the outside of the polymerization apparatus are brought into contact with the aqueous solution during a polymerization, and assuming that a controlled temperature of the liquid contact part is set as TS, a temperature of the gas part is set as TG, and TT is (TS+TG)/2, the polymerization is carried out under temperature conditions satisfying the following equations 1 to 3.

$$35°\text{C} \leq TS \leq 85°\text{C} \qquad \text{Equation 1}$$

$$40°\text{C} \leq TG \leq 90°\text{C} \qquad \text{Equation 2}$$

$$47°\text{C} \leq TT \leq 73°\text{C} \qquad \text{Equation 3}$$

The polymerization apparatus refers to an apparatus for producing a water absorbent resin by using the aqueous solution as a base material through a polymerization, and may include a tank for measuring and keeping monomers or other secondary components, and a polymerization initiator, and a preparation tank for mixing the components, in addition to the polymerization part for polymerization. Typical examples of the polymerization apparatus may include, but may not be particularly limited to, a continuous belt polymerization apparatus as described in FIG. 1 of Patent Literature 3 or FIG. 1 of Patent Literature 36 and a continuous kneader polymerization apparatus as described in FIG. 1 of Patent Literature 43.

The polymerization part refers to a part where a temperature is adjusted so as to satisfy all the Equations 1 to 3 and a polymerization is carried out, but does not refer to a part, like the mixing tank, where polymerization is not carried out.

Figure 1:
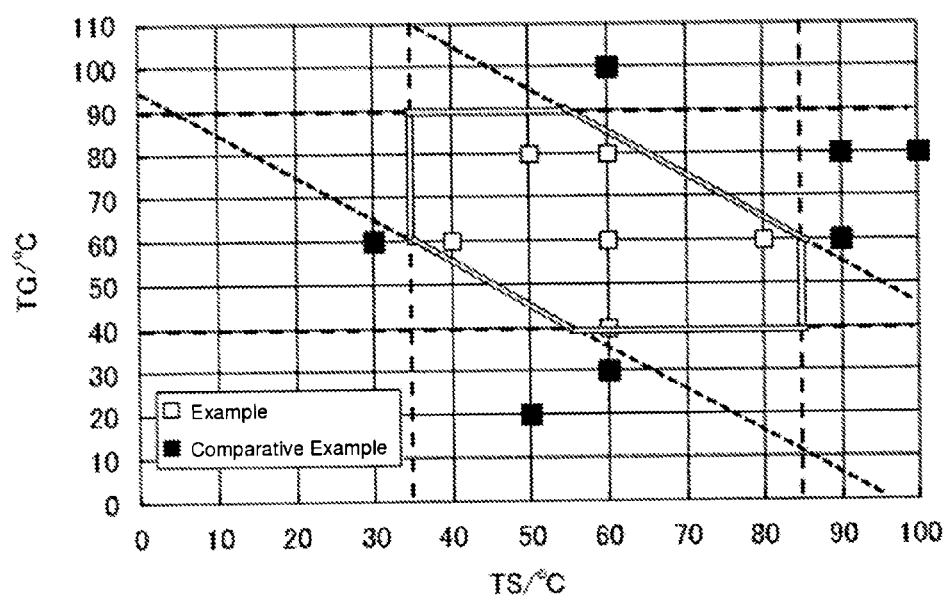
FIG. 1 is a graph illustrating TS and TG in the Examples and Comparative Examples.

Further, the polymerization part is covered with the case so as to prevent a gas in contact with an aqueous solution during polymerization from being freely diffused to the outside of the polymerization apparatus except from the gas supply port and the gas discharge port. Further, the case may be integrated with the polymerization part, or may cover the entire polymerization part as illustrated in FIG. 1 of Patent Literature 36.

The supply line is not particularly limited in configuration as long as it can supply a liquid. The supply line is not limited to be provided at one place, and may be provided at two or more places. If multiple supply lines are provided, they may be configured to supply different base materials, such as for a monomer, a polymerization initiator, a reducing agent (for redox type initiator), an aqueous solution containing a monomer and a polymerization initiator (such as persulfate), and the like to the polymerization apparatus.

The external gas supply port is not particularly limited in configuration as long as it can bring a gas having a predetermined temperature, particularly a temperature-controlled gas, into contact with the aqueous solution during polymerization in the polymerization part so as to satisfy the above-described Equations 1 to 3. Further, the external gas supply port is not limited to be provided at one place, and may be provided at two or more places. If multiple external gas supply ports are provided, gases may be different from each other and may have different temperatures.

The external gas may be supplied by gas supply or suction, or a combination of gas supply and suction, either under pressure or under reduced pressure. The above expression "the external gas is supplied by gas supply" refers to a method of introducing a gas having a predetermined temperature into the polymerization part by forcibly supplying the gas with an air blower from the external gas supply port into the polymerization part so as to control a gas part to have a predetermined temperature. Further, the expression "the external gas is supplied by suction" refers to a method of introducing a gas having a predetermined temperature into the polymerization part by exhausting gas introduced through the external gas supply port or steam generated by polymerization or a monomer component such as volatilized acrylic acid through an exhauster from the gas discharge port so as to control a gas part to have a predetermined temperature.

The gas discharge port refers to a part through which the gas in contact with an aqueous solution during polymerization is discharged to the outside of the polymerization apparatus. As for a continuous polymerization apparatus, the gas discharge port may also serve as a discharge port of a polymerization product. The gas discharge port may be a simple exhaust port or may include a forced exhaust system. A gas discharged through the gas discharge port may be discarded, or may be reused or concentrated. Steam or acrylic acid may be cooled or collected with an alkali so as to be reused, or an inert gas or air may be appropriately adjusted to a predetermined temperature (TG) or to have a predetermined composition so as to be reused.

Further, in the continuous polymerization apparatus, the external gas supply port and the gas discharge port may preferably be arranged such that the former is close to an inlet side and the latter is close to an outlet side. Furthermore, the external gas supply port and the gas discharge port are not particularly limited in position, and may be provided at any position on the up and down sides, the front and back sides, or the right and left sides of the polymerization apparatus. The external gas supply port and the gas discharge port may be more than one, respectively, and may be different in number. That is, a gas flows above a polymer that moves within a polymerization part such as a belt or a kneader, and preferably flows in a reverse direction or in a parallel direction relative to the movement direction of the polymer, and more preferably, in the parallel direction.

The liquid contact part refers to a contact area of a solution (an aqueous solution containing acrylic acid and/or acrylate, a cross-linking agent, and a polymerization initiator, as a monomer component. Hereinafter, it may be referred to as an "aqueous monomer solution") containing all components required for the polymerization. For example, if a polymerization initiator (which includes a reducing agent to be used in redox type initiator, and may be simply referred to in a "polymerization initiator" hereinafter) is added later, the liquid contact part refers to a contact part with the solution at the time when the addition of the polymerization initiator is completed.

The controlled temperature TS refers to a controlled temperature of the liquid contact part but does not refer to a temperature of the aqueous solution in the polymerization part. For example, in the case of batch polymerization, it refers to a temperature of a polymerization apparatus before an aqueous monomer solution is supplied. If necessary, a temperature may be controlled by an air current in an upper space or heating or cooling of a jacket of the apparatus or a rear surface of a belt. In the case of continuous polymerization, it can be appropriately controlled by heating with polymerization heat or heating or cooling the polymerization apparatus with washing water, in addition to the above-described heating or cooling method. It is a temperature of surface in equilibrium at a part serving as the liquid contact part during polymerization after sufficient time with nothing to be supplied to the polymerization part. Further, the TS may be measured with a contact thermometer such as a thermocouple thermometer, or with a non-contact thermometer such as an infrared radiation thermometer.

A temperature TG of the gas part (gas) refers to a temperature (equilibrium temperature) in an atmosphere at a time point (position) where a gas supplied from the outside is supplied into the polymerization part when a polymerization is started, and a temperature obtained when a gas within the polymerization part is mixed with a gas (preferably, warm air) supplied from the outside while being introduced into the polymerization part within the polymerization apparatus and reaching a polymerization starting point within the polymerization part in some cases. The TG may be affected by a temperature of the aqueous monomer solution or steam within the polymerization part, but may be mainly controlled by adjusting a temperature of a gas supplied from the outside (preferably, in the range of the TG). Further, in the case of continuous polymerization, a temperature of the gas part may be increased due to polymerization heat after the polymerization starting point and a temperature of the gas part may be varied depending on a position of the polymerization apparatus at the same time. However, in the present invention, the important thing is the temperature (TG=40 to 90° C.) at the polymerization starting point but not a temperature of a gas varying as a polymerization proceeds (for example, an increased temperature in an upper space due to generation of steam during polymerization, or in the case of a continuous polymerization, a gas temperature above gel generated at the polymerization part). That is, in the present disclosure, it is important to control the temperature TS of the polymerization apparatus in contact with the aqueous monomer solution, the temperature TG of the gas part, and TT. It is noted in Comparative Examples 8 and 9 to be described below that a temperature of a polymerization part, a temperature of a gas part, in contact with polymerized gel during a polymerization, and the arithmetic mean of the two temperatures do not exhibit the effects by the present disclosure. The TS can be measured by installing a thermometer at a predetermined position or collecting a gas from a predetermined position.

Further, in the case of supplying plurality kinds of gases having different temperatures, the TS refers to a temperature when all of the gases supplied are mixed in an adiabatic state and reach equilibrium. For example, if the same gas is supplied at 50° C. at 10 $Nm^3$/hr ($Nm^3$ indicates a volume in a normal state (standard temperature and pressure: 273.15 K 100 kPa). The same shall apply hereafter) and at 60° C. at 15 $Nm^3$/hr, TS is calculated to be $(50 \times 10 + 60 \times 15)/(10+15) = 56°$ C. Further, a gas within the polymerization part may not be 100% substituted with a gas supplied in some cases, but it can be defined as a temperature TG in equilibrium caused by supply of a gas having a predetermined temperature. An rate ($m^3$/min) of a gas supplied may be appropriately selected depending on a temperature of the gas or a temperature in the polymerization apparatus and a volume ($m^3$) of the upper space. Typically, the rate ($m^3$/min) of a gas supplied may be appropriately selected from 0.001 to 100 times or 0.01 to 10 times per minute relative to the volume of the gas part (upper space) in the polymerization part, and to be specific, the rate may be in the range of 0.01 to 1000 $m^3$/min, 0.1 to 100 $m^3$/min, or 1 to 50 $m^3$/min.

The gas supplied may be warm air, or warm air having TG of 40 to 90° C. As described above, the gas may be air, an inert gas, or a mixture thereof, and particularly, may contain air as a main component. For gas supply and suction, a well-known device may be used and the device may be provided with a heat exchanger.

Further, in a method for performing polymerization in a boiling state (Patent Literatures 6 to 8, Patent Literatures 36 to 41) as a conventional technique, continuous belt polymerization or batch polymerization on a hot plate at a surface temperature of 100° C. (corresponding to the TS of the present disclosure) is disclosed, but a temperature or flow of an upper gas in a polymerization area is not adjusted (typically, if a temperature is not disclosed, TG can be understood to be room temperature). The feature of the present invention is to suppress a generation amount of fine powders of a water absorbent resin and attain high absorption property by controlling TG as described above and further necessarily controlling TS in the range of 35 to 95° C. As described in Comparative Examples 10 to 14 to be described below, even in the case of a continuous belt polymerization apparatus as described in FIG. 1 of Patent Literature 36, generation of steam caused by polymerization heat can be seen around a peak polymerization temperature (for example, when polymerized gel is expanded), a temperature TG at a monomer supplying point is a substantially atmospheric temperature (room temperature) and the polymerization is not carried out at TG of 40 to 90° C.

The TT is an arithmetic mean of the controlled temperature TS and the temperature TG of the gas part (gas).

The Equation 1 defines a range of the controlled temperature TS from 35° C. to 85° C. including 35° C. and 85° C., and more preferably, from 50° C. or higher to 70° C. or lower.

The Equation 2 defines a temperature TG of a gas part (gas) in the range of from 40° C. to 90° C. including 40° C. and 90° C., and more preferably, from 50° C. or higher to 90° C. or lower.

The Equation 3 defines a range of the TT from 47° C. to 73° C. including 47° C. and 73° C., and more preferably, from 55° C. or higher to 65° C. or lower.

Further, it was found that when a temperature of the aqueous solution is controlled after the Equations 1 to 3 are satisfied, a better result can be obtained.

That is, during the polymerization step, a temperature TW of the aqueous solution to be supplied to the polymerization part is preferably from 40° C. or higher to lower than 100° C. The temperature may be more preferably 50° C. or higher, still more preferably 60° C. or higher, more preferably 90° C. or lower, and still more preferably 80° C. or lower.

The temperature TW of the aqueous solution refers to a temperature at the time when the aqueous solution is supplied to the polymerization part (before the aqueous solution is brought into contact with the polymerization part). If the aqueous solution is prepared and immediately supplied to the polymerization part, the temperature TW is the same as the temperature at the time of preparation. If the aqueous solution is prepared and then reserved in a reserve tank and the like, the temperature TW refers to a temperature at the time when the aqueous solution is actually supplied.

Further, if the aqueous solution is prepared in the polymerization part by using the multiple supply lines, the temperature TW of the aqueous solution is a temperature of a liquid at the time when all of the base materials are completely supplied (the temperature TW of the aqueous solution in the polymerization part may be slightly changed due to the controlled temperature TS of the liquid contact part or the temperature TG of the gas part, and in this case, the temperature TW of the aqueous solution is defined to be a temperature at the time when the supply is completed).

Furthermore, it has been found that as for the aqueous solution that contains a polymerization initiator as necessary, it is important to maintain the temperature TW of the aqueous solution at a predetermined value or more until a polymerization is started.

That is, during the polymerization step, preferably, the temperature TW of the aqueous solution may not be lower than 40° C. over a period from the preparation of the aqueous solution to the start of polymerization. The temperature TW may be more preferably 50° C. or higher, still more preferably 60° C. or higher, preferably 90° C. or lower, and more preferably 80° C. or lower. Within this range, it is possible to improve physical properties by uniformization in polymerization and also possible to suppress an increased amount of fine powders generated by process damage due to excessive foaming after drying and pulverization.

Further, an area of the polymerization apparatus in contact with the aqueous solution is important. A weight of the aqueous solution per unit area of the liquid contact part (a weight of the aqueous solution per unit area of a site of the polymerization part in contact with the aqueous solution) may be in the range of preferably 6.2 to 23.4 kg/m$^2$ and more preferably 10.0 to 16 kg/m$^2$. In the above-described range, the polymerization can be stably carried out without being affected by a surrounding environment, and deterioration in physical properties or an increase in generation amount of fine powders can be suppressed by appropriately removing polymerization heat.

When the unit area is calculated, it is not an area calculated from a size of an outer shape of the polymerization apparatus, but a total area of an actual site in contact with the solution.

For example, if a contact surface has a curved structure or a wave pattern, or has a structure including an inner partition, a contact area needs to be calculated considering the structure, but it is not necessary to consider change in a contact part caused by expansion or contraction of gel obtained by polymerization. Further, it is not necessary to consider a blade for stirring the aqueous solution for the contact area.

Also, in the case of using a continuous polymerization apparatus, a weight of the aqueous solution per unit area of the liquid contact part (a weight of the aqueous solution per unit area of a site of the polymerization part in contact with the aqueous solution) can be calculated by the following Equation 4.

$$Fw \times t \div S(h0) \qquad \text{Equation 4}$$

Wherein, each parameter of the Equation 4 is defined as follows. Further, the term in brackets denotes a dimension of unit.

h0: h (length) satisfying $V(h)=Fw \times t \div \rho$
Fw: Supply rate (weight/time) of the aqueous solution
$\rho$: Specific gravity (weight/volume) of the aqueous solution at a certain temperature
t: Process time (time)
h: Height of a liquid surface (length)
V(h): Volume of the polymerization part at a height (h) of a liquid surface (volume)
    Volume only when expansion or contraction caused by a polymerization is not carried out
S(h): Contact area (area) of the polymerization part at a height (h) of a liquid surface
    It is an area on the assumption that there is no expansion or contraction caused by a polymerization Further, the V(h) and the S(h) may be values based on the actual measurement, and may be calculated from the drawings if a structure is simple.

For example, if the aqueous solution is brought into contact with a side surface (inner surface) of a continuous polymerization apparatus by using the continuous polymerization apparatus in which a polymerization part has a width of 1 m and a height of 0.05 m, and a distance from a supply line to a polymerization product discharge port of 5 m under conditions that a supply rate (Fw) is 10 kg/min, a specific gravity ($\rho$) of the aqueous solution is 1.01 kg/L, and a process time (t) of the aqueous solution is 5 min, h0 is calculated to be 9.9 mm by the formula: $V(h)=h \times 1$ m$\times 5$ m=10 kg/min÷1.01 kg/L$\times 5$ min, and S(h0) to be $(2 \times h0+1$ m$) \times 5$ m=5.01 m$^2$. From the values, a weight per unit area is calculated to be 10 kg/min$\times 5$ min÷5.01 m$^2$=9.98 kg/m$^2$.

Further, the shortest distance from a certain point within the aqueous solution in the polymerization part to the liquid contact part or part in contact with the gas is preferably at most 280 mm or less, more preferably at most 100 mm or less, more preferably at most 50 mm or less, and most preferably at most 25 mm or less. In this case, a distance becomes 0 mm at the certain point in contact with the liquid contact part. Also, a lower limit may be appropriately determined depending on a shape (a belt shape, a box shape, a tank shape, a cylinder shape, a kneader shape) of the polymerization apparatus or a production amount, and may be preferably 1 mm or more, more preferably 2 mm or more, and more preferably 4 mm or more.

Further, if a content of monomer in the aqueous solution is low, sufficient performance cannot be obtained. Therefore, an adequate concentration is needed.

That is, a water content PW (Pre Water) in the aqueous solution may be preferably 70 wt % or less. Herein, a lower limit of the water content PW in the aqueous solution is not particularly limited, and may be preferably 30 wt % or more from the viewpoint of removing polymerization heat. Further, if a polymerization initiator, water, or another component are further added to the polymerization apparatus so as to be mixed with an aqueous monomer solution to be supplied to the polymerization apparatus, the water content PW in the aqueous solution is defined to be a water content after mixing.

Further, in order to remove polymerization heat (for example, in the case of acrylic acid, 18.5 cal/mol (25° C.)) generated by polymerization, it is desirable to generate steam (water vapor, or another steam of monomer) in an adequate amount. It is desirable to remove polymerization heat from evaporative latent heat and control TG at the same time.

That is, preferably, due to water evaporation as a main factor, a difference (PW−AW) between a water content PW in the aqueous solution and a water content AW (After Water) of a polymerization product obtained at the time when the polymerization step is completed may be 5 wt % or more, or 8 wt % or more.

Herein, an upper limit of the difference (PW−AW) between the water content PW in the aqueous solution and the water content AW of the polymerization product obtained at the time when the polymerization step is completed is not particularly limited, and may be preferably 70 wt % or less, more preferably 50 wt % or less, and more preferably 30 wt % or less, in order to avoid overheating during a polymerization. Further, the water content AW of the polymerization product, although depending on the PW, may also be the upper limit of the PW or less, preferably 10 to 70 wt %, more preferably 15 to 65 wt %, and more preferably 30 to 55 wt %.

An amount of water contained in the polymerization product can be adjusted by adjusting an amount of the gas supplied or humidity.

The polymerization may be a batch reaction or a continuous reaction, and the continuous reaction is more desirable from an industrial point of view. More preferably, the polymerization apparatus may be of continuous kneader type or continuous belt type. The continuous kneader polymerization (stirring polymerization) is disclosed in Patent Literatures 8 and 42 to 45, while the continuous belt polymerization (stirring polymerization) is disclosed in Patent Literatures 1 to 7 and Patent Literatures 36 to 41.

According to the method of the present invention, by controlling immediately early temperatures (TG, TS, TT) in polymerization, it is possible to manufacture a water absorbent resin, which will be described below, having improved saline flow conductivity (SFC) with a small generation amount of fine powders.

In the range where TG, TS, and TT satisfy the Equations 1 to 3, if the TT exceeds 73° C., liquid permeability (SFC) is rapidly decreased and a generation amount of fine powders is sharply increased, which is not desirable. Meanwhile, if the TT is lower than 47° C., a generation amount of fine powders is decreased but saline flow conductivity (SFC) is also decreased, which is not desirable.

Further, if the TW at the time when the aqueous solution is supplied to the polymerization part is lower than 40° C., it takes a remarkably long time to complete polymerization, or polymerization is partially started at the liquid contact part having a temperature higher than a temperature of the solution or at a contact part of the gas, resulting in an uneven polymerization product, which is not desirable. Furthermore, if the TW is 100° C. or higher, polymerization is started before the aqueous solution is supplied to the polymerization part, and thus, the effects by the present invention cannot be attained or a monomer is volatilized, resulting in change in its concentration.

If the TW is lowered to lower than 40° C. before the aqueous solution is supplied to the polymerization part, it is necessary to warm the aqueous solution before being supplied, but polymerization may be started during heating or a monomer may be decomposed by undesirable reaction, which is not desirable.

If a weight of the aqueous solution per unit area of the liquid contact part is low (for example, less than 6.2 kg/m$^2$), productivity would be decreased and heat generated by polymerization would be too rapidly removed, and thus, a polymerization rate would be decreased and desired performance may not be attained. Further, if a weight of the aqueous solution is high (for example, more than 23.4 kg/m$^2$), a distance between a liquid center part of the liquid and the liquid contact part and/or a contact surface with the gas would be increased, and polymerization would be carried out at the liquid center part without any effects obtained by adjusting the TG or the TS, and thus, a water absorbent resin that does not sufficiently obtain the effects by the present invention may be produced.

If a water content is high (for example, PW exceeds 70 wt %), that is, a monomer concentration is low, polymerization would not be adequately carried out, and thus, desired performance may not be attained.

A small difference between the PW and the AW (for example, the difference PW−AW is less than 5 wt %), that is, a small amount of water evaporated by a polymerization means that a removal amount of heat generated by the polymerization is small, that is, a temperature in a reaction system is remarkably increased, and thus, desired performance may not be attained.

Further, the present invention can be appropriately applied to polymerization with a polymerization maximum temperature (polymerization peak temperature) of 100° C. or higher, and particularly higher than 100° C. It is possible to reduce fine powders caused by foaming during high-temperature polymerization, and productivity can be increased due to the maximum temperature of 100° C. or higher, and particularly higher than 100° C. In terms of absorption properties, the maximum temperature may be preferably 150° C. or lower, more preferably 140° C. or lower, more preferably 130° C. or lower, more preferably 120° C. or lower, and particularly preferably 115° C. or lower.

Also, the present invention can be appropriately applied to polymerization for a short time. A preferable polymerization time (from polymerization start to polymerization completion), more preferably, a time from when a polymerization is started until when a polymerization peak is ended (when a polymerization peak temperature is shown) is 60 minutes or less, 30 minutes or less, 10 minutes or less, 5 minutes or less, 3 minutes or less, 0.1 minute or more, and 0.5 minute or more. Further, although the polymerization time (minute) may be the same as the polymerization peak time (minute), preferably, the polymerization time is longer than the polymerization peak time. More preferably, a time from when polymerization is started until when polymerization peak is ended (when a polymerization peak temperature is shown) corresponds to about 1/10 to about 9/10 or about 1/5 to about 4/5 of the total polymerization time (minute). The time can be appropriately set depending on PW, TW, GW, TT, or a polymerization initiator and an amount thereof. By polymerization for the above-described period of time, physical properties and productivity can be improved and fine powders can be reduced.

The method of the present invention satisfying the Equations 1 to 3 can increase productivity and enables stable production. Particularly, the polymerization method of the present invention can be widely applied to aqueous solution polymerization, and preferably, it can be appropriately applied to techniques (Patent Literatures 6 to 8 and Patent Literatures 36 to 41) implemented in a boiling state (particularly, a polymerization peak temperature of higher than 100° C.) or started at a high temperature (higher than 40° C.).

In the case of batch polymerization, after polymerization is started, TS, TG, and TT may not be in the above-described ranges, and may be changed or may be the same as those when the polymerization is started. More preferably, the TS is appropriately selected from the range of about 10 to about 100° C., the TG is appropriately selected from the range of about 40 to about 100° C., and the TT is appropriately selected from the range of about 30 to about 100° C.

(Comparison with Conventional Polymerization Method)

In the present invention, the TS, TG, and TT are essentially controlled in the very early polymerization stage as follows.

$$35° C. \leq TS \leq 85° C. \qquad \text{Equation 1}$$

$$40° C. \leq TG \leq 90° C. \qquad \text{Equation 2}$$

$$47° C. \leq TT \leq 73° C. \qquad \text{Equation 3}$$

In the conventional polymerization as described above or below, for example, a technique of lowering a polymerization temperature for a water absorbent resin or controlling a polymerization temperature within a specific range has been disclosed in Patent Literatures 1 to 5. To be specific, Patent Literatures 2 and 3 disclose polymerization in a belt reaction apparatus capable of cooling or heating from its back under air current (for example, increasing a temperature from 10° C. at the beginning of the polymerization to 60° C. thereafter), but does not disclose a temperature TG of the air current. Patent Literatures 4 and 5 disclose a constant-temperature polymerization, and Patent Literature 4 (U.S. Pat. No. 5,380,808 A) and Patent Literature 5 (EP 496067 A2) disclose belt polymerization at a concentration of 55%, a neutralization ratio of 72% with heating up to 50° C. (corresponding to TS) in Example 3, but does not disclose TG. If an inert gas is introduced into a polymerization apparatus from the outside, it can be construed that the introduced gas has room temperature.

Patent Literature 1 discloses a technique in which a difference between a temperature in a gas part and a temperature in a polymerization system is set to be 0.1 to 70° C. (preferably, 0.1 to 10° C.), and discloses Examples in which polymerization is started by introducing a nitrogen gas of 30° C. (corresponding to TG=30° C. as described in the present disclosure).

Further, polymerization for a water absorbent resin in a boiling state is disclosed in Patent Literatures 6 to 8 and Patent Literatures 36 to 40. Patent Literature 6 (U.S. Pat. No. 7,265,190) discloses belt polymerization at a belt temperature of 100° C. (corresponding to TS) in Example 1. Patent Literature 7 (U.S. Pat. No. 6,906,159) discloses kneader polymerization of monomer at a high temperature of 40° C. or higher (corresponding to TW), and discloses a hot plate temperature (corresponding to TS) of 90° C. in Example 1. Further, Patent Literature 8 (U.S. Pat. No. 6,867,269) discloses kneader polymerization of monomer at a high temperature of 40° C. or higher (corresponding to TW), and discloses a jacket temperature (corresponding to TS) of 100° C. in Example 1 and also discloses the same jacket temperature of 95° C. in Example 6. Likewise, Patent Literatures 36 to 40 disclose polymerization on a hot plate or a heating belt in which a surface of a polymerization apparatus (corresponding to TS) is heated to 100 to 101° C. Patent Literatures 42 to 45 disclose continuous kneader polymerization with a heating or cooling jacket. In Patent Literature 42, polymerization heat is removed using evaporative latent heat and an inert gas is introduced to a continuous kneader for the removal.

However, Patent Literatures 1 to 8 and Patent Literatures 36 to 45 do not disclose active recommendation of introduction of a gas or a temperature (TS) of a gas part in a polymerization apparatus, and do not disclose the TS (35° C. $\leq$ TS $\leq$ 85° C.) as specified in the present description or the TG and the TT, and do not suggest the fact that such temperatures affect an amount of fine powder or SFC. If an inert gas is introduced into a polymerization apparatus from the outside particularly in order to remove polymerization heat by air current, it can be construed that a temperature (TG) of the introduced gas is room temperature. Further, Patent Literature 1 discloses a technique of controlling a temperature of a gas part (controlling a temperature difference in a polymerization system to be small in the range of 65 to 95° C. (preferably, 0.1 to 10° C.)), and describes a polymerization starting temperature (similar to TW of the present disclosure) in the range of preferably 10 to 40° C., and more preferably 15 to 30° C., which corresponds to 15 to 30° C. as the TG of the present description.

In the present invention, by means of introducing warm air having a predetermined temperature (40 to 90° C.) to an introduced gas, a temperature of the gas part (TS=40 to 90° C.) can be controlled within a specific range, and particularly, by applying it to the aqueous monomer solution having a high temperature (TW=40° C. or higher and lower than 100° C.), fine powders after drying can be reduced and various physical properties (particularly, liquid permeability (SFC)) can be improved. Preferably, a preferable polymerization peak temperature in the present invention can exceed 100° C. Further, preferably, a gas of a gas part contains air as a main component.

Hereinafter, a method for producing a water absorbent resin of the present invention including other conditions will be described in detail.

The present invention relates to a method for producing a polyacrylic acid (salt)-based water absorbent resin comprising: a polymerization step of supplying as a base material an aqueous solution containing an acrylic acid and/or an acrylic acid salt as a monomer component and polymerizing the monomer in the presence of a polymerization initiator, wherein in the polymerization step, there is used a polymerization apparatus which comprises a polymerization part covered with a case, said polymerization part comprising at least a supply line for supplying the aqueous solution, an external gas supply port, and a gas discharge port, and has a structure that a liquid contact part in contact with the aqueous solution and a gas supplied from the outside of the polymerization apparatus are brought into contact with the aqueous solution during a polymerization, and assuming that a controlled temperature of the liquid contact part is set as TS, a temperature of the gas part is set as TG, and TT is (TS+TG)/2, the polymerization is carried out under temperature conditions satisfying the following Equations 1 to 3, and more adequate temperatures are as described above.

$$35° C. \leq TS \leq 85° C. \qquad \text{Equation 1}$$

$$40° C. \leq TG \leq 90° C. \qquad \text{Equation 2}$$

$$47° C. \leq TT \leq 73° C. \qquad \text{Equation 3}$$

(Water-Soluble Unsaturated Monomer)

An acrylic acid (salt)-based monomer is not particularly limited as long as a water absorbent resin can be obtained through a polymerization. Examples of the acrylic acid (salt)- based monomer may include anionic unsaturated monomers (salts) such as (meth)acrylic acid, maleic acid (anhydride), itaconic acid, cinnamic acid, vinyl sulfonic acid, allyl toluene sulfonic acid, vinyl toluene sulfonic acid, styrene sulfonic acid, 2-(meth)acrylamide-2-methylpropane sulfonic acid, 2-(meth)acryloylethane sulfonic acid, 2-(meth)acryloylpropane sulfonic acid, 2-hydroxyethyl (meth)acryloyl phosphate, and the like; mercapto group-containing unsaturated monomers; phenolic hydroxy group-containing unsaturated monomers; amide group-containing unsaturated monomers such as (meth)acrylamide, N-ethyl (meth)acrylamide, N,N-dimethyl (meth)acrylamide, and the like; and amino group-containing unsaturated monomers such as N,N-dimethylaminoethyl (meth)acrylate, N,N-dimethylaminopropyl (meth)acrylate, N,N-dimethylaminopropyl (meth)acrylamide and the like.

Among them, the water absorbent resin in the present invention is more preferably a water absorbent resin particle formed of a polyacrylic acid (salt)-based cross-linked polymer obtained by polymerizing monomer(s) containing acrylic acid and/or its salt as the water-soluble unsaturated monomer. Herein, the polyacrylic acid (salt)-based cross-linked polymer refers to a cross-linked polymer obtained by polymerizing monomer(s) containing acrylic acid and/or its salt in an amount of 50 mol % or more, preferably 70 mol % or more, and more preferably 90 mol % or more relative to the total monomer(s).

Further, another water-soluble unsaturated monomer may be used in combination of acrylic acid. To be specific, examples of the another monomer may include anionic unsaturated monomers or its salt such as 2-(meth)acrylamide-2-methylpropane sulfonic acid, 2-(meth)acryloylethane sulfonic acid, 2-(meth)acryloylpropane sulfonic acid, and the like; and acrylamide, methacrylamide, methoxy polyethylene glycol (meth)acrylate, and the like.

Preferably, the acrylic acid may be acrylic acid obtained by gas-phase oxidation of propylene or dehydration and oxidation of glycerin, or in a combination thereof.

The acrylic acid salt is neutralized at any timing of before, during, and after the polymerization. Preferably, the acrylic acid salt may be sodium, lithium, potassium, ammonium, amines, and the like. Among them, sodium salt is preferable in view of cost. An amount of the acrylic acid salt (in other words, neutralization ratio) may be preferably 40 mol % or more, more preferably 50 mol % or more, preferably 90 mol % or less, and more preferably 80 mol % or less, relative to the total amount of acrylic acid and acrylic acid salt.

(Polymerization Initiator)

The polymerization initiator may be used by selecting one or more from those typically used for manufacturing a water absorbent resin. Examples of the polymerization initiator may include heat decomposition type initiators (for example, persulfate: sodium persulfate, potassium persulfate, ammonium persulfate; peroxides: hydrogen peroxide, t-butyl peroxide, methyl ethyl ketone peroxide; azo compounds: an azo nitrile compound, an azo amidine compound, a cyclic azo amidine compound, an azo amide compound, an alkyl azo compound, 2,2'-azobis(2-amindinopropane)dihydrochloride, 2,2'-azobis[2-(2-imidazolin-2-yl)propane]dihydrochlorid e), and photodecomposition type initiators (for example, benzoin derivatives, benzyl derivatives, acetophenone derivatives, benzophenone derivatives, and azo compounds). Among them, the heat decomposition type initiator can easily exhibit the effects by the present invention (particularly, stability of polymerization) by controlling TG, and also, the heat decomposition type initiator is preferable in view of cost and ability of reducing residual monomer, and particularly, persulfate is preferable. Further, a reducing agent that promotes decomposition of the polymerization initiator may be used in combination with the polymerization initiator so as to be a redox type initiator. Examples of the reducing agent may not be specifically limited but may include (bi)sulfurous acid (salt) such as sodium sulfite, sodium hydrogensulfite, and the like; L-ascorbic acid (salt); reducing metal (salt) such as ferrous salt; amines; and the like. More preferably, the photodecomposition type initiator and the heat decomposition type initiator may be used together. Still more preferably, when the heat decomposition type initiator is mixed with an aqueous solution having the TW, to start polymerization with heat, and to attain the effects by the present invention. An amount of the polymerization initiator to be used is not specifically limited, and may be in the range of typically, 0.001 wt % to 2 wt %, preferably 0.01 to 0.5 wt %, relative to the total amount of monomer in the aqueous solution.

(Internal Cross-Linking Agent)

The aqueous solution contains acrylic acid and acrylic acid salt, the polymerization initiator, and water as essential components. If necessary, the aqueous solution may contain a conventionally well-known internal cross-linking agent. Examples of the internal cross-linking agent may include N,N'-methylenebis(meth)acrylamide, (poly)ethylene glycol di(meth)acrylate, (poly)propylene glycol di(meth)acrylate, trimethylolpropane tri(meth)acrylate, glycerin tri(meth)acrylate, glycerin acrylate methacrylate, ethylene oxide modified trimethylolpropane tri(meth)acrylate, pentaerythritol hexa (meth)acrylate, triallyl cyanurate, triallyl isocyanurate, triallyl phosphate, triallyl amine, poly(meth)allyloxy alkane, (poly)ethylene glycol diglycidyl ether, glycerol diglycidyl ether, ethylene glycol, polyethylene glycol, propylene glycol, glycerin, 1,4-butanediol, pentaerythritol, ethylene diamine, ethylene carbonate, propylene carbonate, polyethylene imine, glycidyl (meth)acrylate, and the like. Among them, one or more agents may be used in consideration of the reactivity. In particular, preferably, a compound with two or more polymerizable unsaturated groups may be used as the internal cross-linking agent.

An amount of the internal cross-linking agent to be used may be suitably determined depending on desired physical properties of the water absorbent resin, and typically, may be in the range of preferably 0.0001 to 10 mol % and more preferably 0.001 to 1 mol %, relative to the total amount of the monomer. If the amount of the internal cross-linking agent used is too small, gel strength would be decreased and extractable content would tend to be increased. On the other hand, if it is too large, water absorption capacity would tend to be decreased.

(Other Additives to the Aqueous Solution)

Besides, a hydrophilic polymer such as starch, a starch derivative, cellulose, a cellulose derivative, polyvinyl alcohol, polyacrylic acid (salt), cross-linked polyacrylic acid (salt); a chain transfer agent such as hypophosphorous acid (salt); or a chelating agent may be added. In the case where the additive is added, an amount of the additive may be in the range of preferably 0 to 30 wt %, more preferably 0.005 to 20 wt % relative to the monomer.

(Preparation of Aqueous Solution)

The aqueous solution may be prepared preferably by mixing and stirring the respective components before they are supplied to the polymerization part, or may be prepared within the polymerization part by supplying a part or all of the components to the polymerization part.

(Polymerization Inhibitor)

Preferably, in order to stably supply a monomer having a predetermined temperature, the monomer in the present invention may contain a polymerization inhibitor, preferably methoxyphenols, particularly p-methoxyphenol, in a predetermined amount. An amount of the polymerization inhibitor may be determined depending on kind or temperature thereof, but may be preferably 200 ppm (relative to monomer) or less, or 10 to 130 ppm, and 20 to 100 ppm. The monomer component to be supplied to the polymerization apparatus may be deoxygenated, particularly substituted with an inert gas if necessary. However, in view of stability of the monomer, preferably, oxygen in a predetermined amount may be contained in addition to the polymerization inhibitor, and may be contained in an amount of 0.1 to 15 ppm, 1 to 10 ppm, and 2 to 10 ppm.

(Polymerization Method)

In the polymerization of monomer containing acrylic acid and/or the salt thereof as main components, bulk polymerization, reversed phase suspension polymerization, and precipitation polymerization can be carried out. In view of performance or easiness of controlling polymerization, aqueous solution polymerization using an aqueous monomer solution is more preferable. Such a polymerization method is disclosed in, for example, Patent Literatures 1 to 8 and Patent Literatures 37 to 42, and also, U.S. Pat. No. 4,625,001, U.S. Pat. No. 4,769,427, U.S. Pat. No. 4,873,299, U.S. Pat. No. 4,093,776, U.S. Pat. No. 4,367,323, U.S. Pat. No. 4,446,261, U.S. Pat. No. 4,683,274, U.S. Pat. No. 4,690,996, U.S. Pat. No. 4,721,647, U.S. Pat. No. 4,738,867, U.S. Pat. No. 4,748,076, and US 2002/40,095 A. Among them, a combination with a technique (Patent Literatures 6 to 8 and Patent Literatures 36 to 41) of polymerization in a boiling state (peak temperature of higher than 100° C.) or a polymerization starting at a high temperature (higher than 40° C.) is preferable.

(Polymerization Apparatus)

The polymerization apparatus used in the present invention may be either of batch type and continuous type as long as it has the above-described function, or may employ a well-known apparatus. Preferably, continuous kneader polymerization or continuous belt polymerization may be used, and more preferably, continuous belt polymerization may be used. In the continuous kneader polymerization, it is necessary to lower a concentration of oxygen in a gas part by using nitrogen as a gas to be supplied from the outside in order to obtain a water absorbent resin having high physical properties. In the continuous belt polymerization, it is not necessary to operate in the same manner, and the latter technique tends to reduce a polymerization time and excels in terms of manufacturing costs or productivity.

(Polymerization Part)

The polymerization part is not specifically limited in configuration as long as it satisfies the above-described configuration including the liquid contact part.

(Liquid Contact Part)

The liquid contact part is not specifically limited in shape. It may be formed of combination of a flat surface and/or a curved surface. If it has a shape which can be visually recognized from a vertical direction relative to a liquid surface in contact with the gas, it is possible to prevent accumulation of the gas when the aqueous solution is supplied, and it is also easy to take out a polymerization product, which is preferable.

Further, a material of a member constituting the liquid contact part is not limited as long as it does not absorb the aqueous solution nor react with the aqueous solution, or is not deteriorated by heat during a polymerization. To be specific, examples thereof may include iron, stainless steel, aluminum, fluorine resin, glass, and the like. A mechanical strength is often required in industrial fields, and from the viewpoint of heat transfer, particularly, a metallic material having a heat conductivity of 1.0 W/m/K or more is preferable. However, elution of a trace amount of metallic element may cause deterioration in performance of a water absorbent resin. Therefore, preferably, a metallic material such as iron, stainless steel, aluminum, and the like may be coated in a thickness of 5 mm or less with a chemically and thermally stable fluorine resin or silicon rubber only, polyvinyl chloride or polyphenylene sulfide, or a fluorine resin or silicon rubber containing glass fiber.

(Temperature Control)

The polymerization part includes a means for controlling a temperature during polymerization. Preferably, the means may use the electric heater, steam, hot water, and the like as a heat source. Hot water is preferable from the viewpoint of safety and the range of controlled temperature.

(Gas Supplied from the Outside)

A gas supplied from the outside to the polymerization part may have a relative humidity of 70% or less at a temperature (TG) of the gas part (gas), and may be preferably air or an inert gas (nitrogen, water vapor, and the like) or a mixture thereof. Since there is small influence of a polymerization inhibition caused by oxygen within the polymerization part, use of air or a mixed gas containing air as a main component (50 vol % or more, or 70 vol % or more) is preferable in view of cost.

(Another Accessory Equipment in the Polymerization Apparatus)

The polymerization apparatus may include a tank for measuring and keeping monomer component or another accessory component, a polymerization initiator, and the like, or a mixing tank for mixing such components, as well as the polymerization part for polymerization.

(Method of Controlling Temperature of Aqueous Solution)

The temperature (TW) of the aqueous monomer solution can be achieved by a method of mixing the respective components controlled to adequate temperatures or a method of using heat generated during preparation. Further, the temperature (TW) of the aqueous solution is controlled so as not to be preferably lower than 40° C. over a period from the preparation of the aqueous solution to the start of polymerization, and more preferably not lower than 50° C. by preparing the aqueous solution to have a temperature of 50° C. or more. Furthermore, within 1 minute after the polymerization initiator is added, more preferably within 30 seconds, more preferably within 5 seconds, and more preferably within 2 seconds (lower limit is more than 0 second and preferably, 0.1 second or more), the aqueous solution may be supplied to the polymerization part. The too long period would cause a problem with stability of the monomer depending on a temperature or an initiator, and the too short period would cause insufficient mixture with a polymerization initiator.

(Amount of Aqueous Solution to be Supplied)

A too large amount of the aqueous monomer solution to be supplied to the polymerization part would cause great difference in heat transfer through heating or heat removal between at an outer peripheral part and at a central part of the aqueous solution during polymerization, to obtain as a water absorbent resin obtained by the polymerization a mixture of polymers different in performance, which is not preferable. Further, a too small amount would induce decrease in polymerization rate or remarkable reduced volatile components such as water due to increase of heat removed by the polymerization than that generated by the polymerization, which is not preferable.

(Method of Supplying Aqueous Solution)

In the case of a batch type polymerization apparatus, polymerization can be carried out in such a state as that the aqueous solution is supplied to the polymerization part and then the reaction apparatus is covered with a case, or a polymerization chamber to which the aqueous solution has been supplied is provided within the polymerization apparatus covered with a case. Further, in the case of a continuous type polymerization apparatus, polymerization can be carried out by continuously supplying the aqueous solution to the polymerization part through a pipe and the like.

(Water Content in Aqueous Solution)

If a water content (PW) in the aqueous solution is too high, heat transfer or transfer of a material may be inhibited during polymerization, and it may not be suitable for obtaining a uniform polymerization product. Further, since a final product is dried so as to have a water content of 15 wt % or less, or 10 wt % or less, if unnecessary water is contained, a great amount of heat may be needed for a drying step. Therefore, it is not industrially preferable in view of deterioration during a drying step or cost for a drying step.

(Water Content in Polymer)

Further, a part of heat may be preferably removed during polymerization by generating water vapor. Preferably, a difference (PW−AW) between a water content (PW) in the aqueous solution and a water content (AW) of a polymerization product obtained at the time when the polymerization step is completed may be 5 wt % or more. For example, a decreased amount of water can be controlled by controlling a flow rate of the gas.

(Industrial Polymerization Apparatus)

Preferably, the polymerization apparatus may be of continuous kneader type or continuous belt type from an industrial view. A well-known polymerization apparatus may be used as long as it can satisfy each of the above-described requirements.

(Post-Process)

The polymerization product (hereinafter, referred to as "a water-containing gel-like crosslinked polymer") obtained by the polymerization step can be subjected to the following steps such as gel crushing, drying, pulverizing, classification, fine powder recycle (preferably, agglomeration), and surface cross-linking, to obtain a product having a desired shape and desired physical properties. Among them, the water-containing gel-like crosslinked polymer is preferably subjected to a drying step, a pulverizing step, and a surface cross-linking step, and/or a fine powder recycling step. That is, the method of the present invention may further comprise a drying step, a pulverizing step, and a surface cross-linking step, or may further comprise a fine powder recycling step.

(Gel Agglomeration Step)

The water-containing gel-like crosslinked polymer obtained by the polymerization step may be aged or heated, or dried as it is after polymerization. Preferably, during polymerization or after polymerization, the water-containing gel-like crosslinked polymer may optionally be gel-crushed with a cutter or a crusher (kneader, meat chopper, and the like), to obtain a particle. That is, the gel agglomeration (gel crushing) step may be further included between the polymerization step by continuous belt polymerization or continuous kneader polymerization and the drying step.

A temperature of the water-containing gel-like crosslinked polymer at the time when the gel is crushed during polymerization or after polymerization (particularly, after polymerization) is controlled to be 100° C. or lower, preferably 10 to 95° C., more preferably 20 to 90° C., and more preferably 30 to 85° C., or 40 to 80° C. in view of physical properties. Further, if the gel is crushed during polymerization such as kneader polymerization, a gel-crushing temperature may vary depending on a polymerization rate, but the gel-crushing may preferably performed at the temperature within this range for 50% or more, or 70% or more of the entire polymerization step (total polymerization time).

A resin solid content of the water-containing gel-like crosslinked polymer (hydrogel) is not specifically limited but may be determined mainly depending on AW, and may be preferably 10 to 70 wt %, more preferably 15 to 65 wt %, and more preferably 30 to 55 wt %, from the viewpoint of physical properties. Water, polyhydric alcohol, a mixed liquid of water and polyhydric alcohol, a solution of a polyvalent metal in water, or their steam, and the like may be added to the hydrogel.

A weight average particle diameter (defined by sieve classification) of the particulate hydrogel after the gel-crushing may be in the range of preferably 0.2 to 10 mm, more preferably 0.3 to 5 mm, and particularly preferably 0.5 to 3 mm. Further, particles having a particle diameter of 5 mm or more may be contained in an amount of preferably 0 to 10 wt % and more preferably 0 to 5 wt % of the entire particulate hydrogel. Further, the particle diameter of the particulate hydrogel can be fixed by a wet classification method as described in paragraph [0091] in JP 2000-063527 A.

(Drying Step)

In the drying step, the water-containing gel-like crosslinked polymer obtained by the above-described polymerization step may be dried by using hot air, to obtain a dried cross-linked polymer. Further, before the drying step, the water-containing gel-like cross-linked polymer is crushed to an adequate size, so as to improve efficiency of the drying step or subsequent pulverizing step.

The drying step may be carried out by flowing hot air having a temperature of 120° C. to 250° C. and more preferably 150° C. to 200° C. A flow rate and time of the hot air may be adequately set depending on a water content and total weight of the water-containing gel-like cross-linked polymer, and a required drying state thereof. A water content (ERT 430.2-02) is typically 15% or less, a moisture content after drying is 10% or less, or 8% or less, and particularly preferably 5% or less. Particularly preferably, a drying step of a water absorbent resin using a traverse conveyor disclosed in the WO 2012/144595 A may be carried out.

Further, before the drying step, the water-containing gel-like cross-linked polymer may be crushed for uniform drying or improvement in drying efficiency.

(Pulverizing and Classification Step)

The pulverizing step may be adequately selected from those conventionally known in the art depending on a shape or hardness of the dried cross-linked polymer obtained by the drying step, and a particle size of a targeted pulverized product. Further, if it is possible to crush to a desired size in the classification step before the drying step, the pulverizing step may not be needed.

The powder obtained by the pulverizing step may be subjected to classification step with a sieve capable of obtaining a desired particle size by using Patent Literatures 30 to 35. A great amount of fine powders passing through a sieve with a mesh size of 150 μm would induce generation of dust in a subsequent step or later, and thus the fine powders may be preferably removed. As described above, according to the present invention, a generation amount of the fine powders after drying and pulverizing can be reduced. To be specific, a generation amount of fine powders (particles of 150 μm or less) after drying and pulverizing may be preferably 0 to 30 wt % and more preferably 5 to 25 wt %, relative to the total amount of the pulverized product.

An adequate particle size is in the range as described in the following paragraph (d) "PSD" (ERT 420.2-02), and preferably, the particle size is controlled in the above-described range during the pulverizing step or classification step before the surface cross-linking step, and more preferably, a classification step (second classification step) is included even after the surface cross-linking step.

(Fine Powder Recycling Step)

The fine powder (fine powder containing particles passed through a mesh of 150 μm as a main component, particularly in an amount of 70 wt % or more) removed by the classification step can be optionally subjected to fine powder recycling step, and the recycled fine powder may be subjected to fine powder agglomeration step to re-use the fine powder, which is desirable from industrial view. The fine powder recycling step is described in, for example, Non-Patent Literature 1 or Patent Literatures 25 to 29, and the recycling step is carried out during the polymerization step, the gel pulverizing step, and the drying step before the classification step so that the fine powder can be recycled, which can also be carried out according to, for example, a method of Granulation Example 1 described in Patent Literature 29 (U.S. Pat. No. 6,228,930). The recycled fine powder product, for example, agglomerated fine powder, can be subjected to above-described drying, pulverizing, and classification step, to obtain a (agglomerated) water absorbent resin having a particle diameter greater than that of fine powder. Further, in the case of using the recycled (for example, agglomerated) water absorbent resin, it may be mixed with a water absorbent resin which is not classified as fine powder during the classification step. If a fine powder is recycled during the polymerization step, the fine powder may be mixed with a monomer before polymerization, or may be mixed with a hydrogel during polymerization. The former case can be appropriately applied to calculation of PW (%) as described above.

Physical properties of the particle size of the water absorbent resin, for example, a weight average particle diameter (D50) or a logarithmic standard deviation (σ) of particle size distribution, are not specifically limited, and may be preferably in the range as described in the following paragraph (d) "PSD" (ERT 420.2-02). After the mixing step, or after the classification step if the agglomerated water absorbent resin is not used, the water absorbent resin may be a target.

(Surface Cross-Linking Step)

Further, by performing a surface cross-linking step, a surface-treated water absorbent resin can be obtained. In this case, since the water absorbent resin can be combined through the surface cross-linking step, a required water absorbent resin can be obtained by appropriate classification as needed. Various physical properties of a desirable water absorbent resin are controlled by the following (a) to (e). For example, the water absorbent resin can show both high water absorption capacity of CRC 25 and high liquid permeability of SFC 95.

(Surface Cross-Linking Agent)

In the surface cross-linking step, various organic surface cross-linking agents or inorganic cross-linking agents may be used as a surface cross-linking agent. From viewpoint of physical properties or processability, an organic surface cross-linking agent capable of reacting with a carboxyl group is preferably used. Examples of the organic surface cross-linking agent may include polyhydric alcohol compounds, epoxy compounds, haloepoxy compounds, polyvalent amine compounds or their condensation products with haloepoxy compounds, oxazoline compounds, mono-, di-, or poly-oxazolidinone compounds, polyvalent metal salts, alkylene carbonate compounds, cyclic urea compounds, and the like. For improvement in liquid permeability, one or more of polyhydric alcohol compounds, alkylene carbonate compounds, oxazolidinone compounds, and epoxy compounds may be preferably used, and an inorganic surface cross-linking agent (ionically surface cross-linking agent) may be more preferably used together with or independently from the organic surface cross-linking agent.

(Organic Surface Cross-Linking Agent)

Typically, those conventionally well-known in the art as described in U.S. Pat. Nos. 6,228,930, 6,071,976, and 6,254,990 or reaction conditions thereof (a reaction temperature, a solvent, a mixer, and a heater) may be used. More typically, examples thereof may include polyhydric alcohol compounds such as ethylene glycol, propylene glycol, diethylene glycol, triethylene glycol, tetraethylene glycol, polyethylene glycol, 1,3-propanediol, dipropylene glycol, 2,2,4-trimethyl-1,3-pentanediol, polypropylene glycol, glycerin, polyglycerin, 2-butene-1,4-diol, 1,4-butanediol, 1,3-butanediol, 1,5-pentanediol, 1,6-hexanediol, 1,2-cyclohexanedimethanol, 1,2-cyclohexanediol, trimethylolpropane, diethanolamine, triethanolamine, polyoxypropylene, oxyethylene-oxypropylene block copolymer, pentaerythritol, sorbitol, and the like; expoxy compounds such as ethylene glycol diglycidyl ether, polyethylene glycol diglycidyl ether, glycerol polydiglycidyl ether, diglycerol polydiglycidyl ether, polyglycerol polydiglycidyl ether, propylene glycol diglycidyl ether, polypropylene glycol diglycidyl ether, glycidol, and the like; polyvalent amine compounds such as ethylene diamine, diethylene triamine, triethylene tetramine, tetraethylene pentamine, pentaethylene hexamine, polyethylene amine, polyamide polyamine, and the like, or their inorganic salts or organic salts (aziridinium salt, etc.); haloepoxy compounds such as epichlorohydrin, epibromohydrin, α-methyl epichlorohydrin, and the like; condensation products of the polyvalent amine compounds with the haloepoxy compounds; oxazolidinone compounds such as 2-oxazolidinone (exemplified in U.S. Pat. No. 6,559,239); alkylene carbonate compounds such as ethylene carbonate; oxetane compounds (exemplified in US 2002/72,471 A); cyclic urea compounds such as 2-imidazolidinone; and the like; polyvalent isocyanate compounds such as 2,4-tolylenediisocyanate, hexamethylene diisocyanate, and the like; polyvalent oxazoline compounds such as 1,2-ethylenebisoxazoline, and the like; and alkylene carbonate compounds such as 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxane-2-one, 4-methyl-1,3-dioxane-2-one, 4,6-dimethyl-1,3-dioxane-2-one, 1,3-dioxopan-2-one, and the like.

(Inorganic Surface Cross-Linking Agent)

An inorganic surface cross-linking agent may be used as an ionically surface cross-linking agent or together in combination with an organic surface cross-linking agent, so as to improve liquid permeability and absorption rate. Examples of the inorganic surface cross-linking agent may include polyvalent metallic compounds containing zinc (Zn), calcium (Ca), magnesium (Mg), aluminum (Al), iron (Fe), zirconium (Zr), and the like.

Inorganic surface cross-linking agents to be used may be salts (organic salts or inorganic salts) or hydroxides of polyvalent metals, such as preferably, bivalent metals and more preferably, trivalent or tetravalent metals. Examples of available polyvalent metals may include aluminum, zirconium, and the like, and may include aluminum lactate or aluminum sulfate. Preferably, an aqueous solution containing aluminum sulfate may be used. These inorganic surface cross-linking agents may be used together with or independently from an organic surface cross-linking agents. Surface cross-linking with a polyvalent metal is disclosed in WO 2007/121037 A, 2008/09,843 A, and 2008/09,842 A, and U.S. Pat. Nos. 7,157, 141, 6,605,673, and 6,620,889, and US 2005/0,288,182 A, US 2005/0,070,671 A, US 2007/0,106,013 A, and US 2006/0,073,969 A.

(Other Additives to Surface Cross-Linking Agent)

Likewise, inorganic particles may be used, and for example, silicon dioxide is preferable as exemplified in U.S. Pat. No. 7,638,570. As a preparation method of the present disclosure, a method for producing a water absorbent resin comprising a step of adding any one or more of the polyvalent metals, cationic polymers, and inorganic particles is preferable. Further, organic acid (salt) such as lactic acid (for example, sodium lactate), inorganic acid (salt) such as phosphoric acid, a surfactant, and the like may be added, and an amount thereof is preferably 0 to 2 parts by weight and preferably 0.001 to 1 part by weight.

The cationic polymers (particularly, weight average molecular weight of about 5,000 to about 1,000,000) may be used together with or independently from an organic surface cross-linking agent, so as to improve liquid permeability and the like. Cationic polymers to be used may be preferably, for example, vinyl amine polymer, and are exemplified in U.S. Pat. No. 7,098,284, WO 2006/082188 A, WO 2006/082189 A (Patent Literature 18), WO 2006/082197A (Patent Literature 16), WO 2006/111402A, WO 2006/111403 A, and WO 2006/111404 A.

(Amount of Surface Cross-Linking Agent)

An amount of surface cross-linking agent used may be determined depending on the compounds used or combination thereof, and an amount of organic surface cross-linking agent (and inorganic surface cross-linking agent if used together) may be in the range of preferably 0.001 to 10 parts by weight and more preferably 0.01 to 5 parts by weight, relative to 100 parts by weight of the water absorbent resin.

(Surface Cross-Linking Reaction Condition)

As a solvent, water or a hydrophilic organic solvent may be contained in an amount of 0 to 20 parts by weight, and an amount of the hydrophilic organic solvent may be preferably 0.1 to 10 parts by weight. A reaction temperature may be appropriately determined depending on a kind of a cross-linking agent and may be in the range of 50 to 300° C. and preferably 100 to 200° C.

That is, in order to control liquid permeability (SFC), particle size is controlled as described above after the drying step, and surface cross-linking, preferably surface cross-linking with a covalently surface cross-linking agent and an ionically surface cross-linking agent in combination is carried out, and/or surface cross-linking is carried out by heat treatment at 150 to 250° C. If water absorption capacity (CRC) after surface cross-linking is too high, the SFC would tend to be decreased, and thus, the CRC is preferably 50 [g/g] or less and more preferably 45 [g/g] or less. The CRC can be lowered to of 40 [g/g] or less through surface cross-linking. Further, a lower limit of the CRC is not specifically limited and may be preferably 10 [g/g] or more, more preferably 20 [g/g] or more, more preferably 25 [g/g] or more, and particularly preferably 27 [g/g] or more. For such case, CRC may be lowered by surface cross-linking such that the CRC reduction ratio is 0.1 to 0.9 time, or further 0.5 to 0.85 time, particularly 0.6 to 0.8 time in terms of CRC after and before the surface cross-linking.

In the above-described surface cross-linking step, cross-linking can be carried out by heating and/or irradiation of ultraviolet rays. Conditions of the heating or irradiation of ultraviolet rays can be appropriately selected depending on a kind or amount of a surface cross-linking agent to be used, and physical properties of a target cross-linked water absorbent resin.

(Other Steps)

In addition to the surface cross-linking step, various modifying agents may be added to a certain step. Further, after surface cross-linking, an agglomeration step, a classification step (second classification step), a fine powder removal step, or a fine powder recycling step (after surface cross-linking) may be further carried out to the whole particles so as to attain a desired particle size, and preferably, to attain a particle size distribution as described below. The modifying agents to be used in the present invention may include a chelating agent, a reducing agent such as sulfite and the like, a urine-resistance improving agent, an anti-blocking agent such as a water insoluble particle, a surfactant, water, an anti-coloring agent, a deodorant, an antimicrobial agent, an anti-dust agent, and the like, and may be used in an amount of typically 0 to 5 parts by weight or less, 0.0001 to 1 part by weight, and 0.001 to 0.5 parts by weight, relative to 100 parts by weight of the water absorbent resin depending on its purpose.

(Water Absorbent Resin Obtained)

A method for producing a water absorbent resin of the present invention is suitable for producing a water absorbent resin having the following physical properties (a) to (e).

Particularly, the method makes it possible to reduce a generation amount of fine powders and to improve liquid permeability (without excessively lowering water absorption capacity), and thus, it can be applied to a method for producing a water absorbent resin simultaneously satisfying the physical properties (a), (d), (e) and (b), (c), (f).

(a) CRC (Centrifuge Retention Capacity) (ERT 441.2-02)

A CRC (Centrifuge Retention Capacity) of a water absorbent resin obtained by the present invention is preferably 10 [g/g] or more, more preferably 20 [g/g] or more, more preferably 25 [g/g] or more, and particularly preferably 27 [g/g] or more. An upper limit of the CRC is not specifically limited, and may be preferably 50 [g/g] or less, more preferably 45 [g/g] or less, and more preferably 40 [g/g] or less. The CRC can be appropriately controlled with an internal cross-linking agent or a surface cross-linking agent.

(b) AAP (Absorption Against Pressure) (ERT 442.2-02)

An AAP (Absorption Against Pressure) of the water absorbent resin obtained by the present invention as an AAP under pressure of 4.83 kPa (0.7 psi) by the drying may be preferably 15 [g/g] or more, more preferably 20 [g/g] or more, more preferably 22 [g/g] or more, and even more preferably 24 [g/g] or more, in order to prevent leakage from a disposable diaper. An upper limit of the AAP is not specifically limited, and may be preferably 40 [g/g] or less for balance with other physical properties. When the APP is less than 20 [g/g], such a water absorbent resin, when used in an absorbent body, could not provide a hygiene product having small return of absorbed liquid (typically, referred to as "re-wet") by applying a pressure to the absorbent body, which would not be preferable. Further, the APP can be appropriately controlled with a surface cross-linking agent or a particle size.

(c) "Ext" (ERT 470.2-02)

"Ext" is an abbreviation for extractables, and may be used in an amount of preferably 30 wt % or less, 20 wt % or less, 15 wt % or less, or 10 wt % or less. A lower limit is preferable as low as possible, and may be about 3 wt % in consideration of the other physical properties, particularly CRC. The Ext can be appropriately controlled with an amount of a cross-linking agent during polymerization.

(d) "PSD" (ERT 420.2-02)

A weight average particle diameter (D50) is preferably 100 µm or more to 600 µm or less, more preferably 200 µm or more to 500 µm or less, and more preferably 300 µm or more to 400 µm or less. If the weight average particle diameter (D50) is out of the above-described range, liquid permeability may be decreased and a liquid absorption rate may be remarkably decreased. That is, since the absorption rate (FSR/Vortex) would be greatly decreased, for example, when used in a diaper, leakage of a liquid may occur. Further, particles of 150 µm or more to 710 µm or less account for preferably 50 wt % or more and more preferably 80 wt % or more. Further, a ratio of particles passing through a sieve with a mesh size of 150 µm is preferably 5 wt % or less, more preferably 3 wt % or less, and most preferably 1 wt % or less. If a ratio of the particles passing through a sieve with a mesh size of 150 µm exceeds 5 wt %, there may be safety and hygiene problems caused by scattering of the particles while a water absorbent resin (absorbent body) is produced. Further, physical properties of the absorbent body obtained may deteriorate. Furthermore, a logarithmic standard deviation ($\sigma\zeta$) of particle size distribution is preferably 0.20 or more to 0.50 or less and more preferably 0.30 or more to 0.40 or less. If the logarithmic standard deviation ($\sigma\zeta$) is out of this range, liquid permeability may be decreased and an absorption rate of a liquid to the absorbent body may be remarkably decreased. Although the particle size distribution is controlled in a final product, preferably, the particle size distribution is controlled to be in the above-described range through the pulverizing, classification, and fine powder recycling steps before the surface cross-linking step.

(e) SFC (Saline Flow Conductivity)

An SFC (Saline Flow Conductivity) of the water absorbent resin obtained by the present invention as an SFC that indicates liquid permeability of a liquid under load by the drying may be preferably 1 [$\times 10^{-7} \cdot cm^3 \cdot s \cdot g^{-1}$] or more, and more preferably 10 [same unit] or more, 50 [same unit] or more, 70 [same unit] or more, 92 [same unit] or more, 95 [same unit] or more, 100 [same unit] or more in this order, in order to prevent leakage from a disposable diaper. An upper limit of the SFC is not specifically limited, and may be preferably 3000 [same unit] or less, more preferably 2000 [same unit] or less, more preferably 1000 [same unit] or less, more preferably 500 [same unit] or less, and particularly preferably 300 [same unit] or less for balance with other physical properties. When the SFC exceeds 3000 [same unit], such a water absorbent resin, when used in an absorbent body, would induce leakage of a liquid from the absorbent body, which is not preferable. Further, the SFC can be appropriately controlled by controlling a particle size distribution and a surface cross-linking. In the present specification, unless the unit of SFC is clearly specified, the same unit as described above is applied.

(f) "Moisture Content" (ERT 430.2-02)

"Moisture Content" is in the range of 0.1 to 15 wt % or 0.5 to 10 wt % due to an absorption property and an impact resistance of the water absorbent resin.

(Applications)

A water absorbent resin obtained by the method of the present invention makes it possible to particularly reduce a generation amount of fine powders and to improve liquid permeability (without excessively lowering water absorption capacity). Therefore, it can be widely used for various applications, particularly for a material of hygiene articles such as a disposable diaper.

EXAMPLES

In Examples, physical properties were measured by reference to the EDANA, unless specifically defined otherwise.

"EDANA" and "ERT"

"EDANA" is an abbreviated expression for European Disposables and Nonwovens Associations, and "ERT" is an abbreviated expression for the measurement methods of water absorbent resins (EDANA Recommended Test Methods) under the European standards (approximately the world standards). Additionally, in the present invention, the physical properties of water absorbent resins are measured by reference to the original text of ERT (publicly known literature, revised in 2002), unless specifically defined otherwise.

(a) "CRC" (ERT 441.2-02)

"CRC" is an abbreviation for Centrifuge Retention Capacity and means water absorption capacity without load (hereinafter, sometimes referred to as "water absorption capacity"). To be specific, the CRC is the water absorption capacity (unit; [g/g]) after 0.2 g of a water absorbent resin in a nonwoven fabric bag is freely swollen in a 0.9 wt % aqueous sodium chloride solution present in excess amount for 30 minutes and dehydrated by a centrifuge.

(b) "AAP" (ERT 442.2-02)

"AAP" is an abbreviation for Absorption Against Pressure and means water absorption capacity under load. To be specific, the APP is water absorption capacity (unit; [g/g]) after 0.9 g of the water absorbent resin is swollen in an excess amount of 0.9 wt % aqueous sodium chloride solution for 1 hour under 2.06 kPa (0.3 psi, 21 [g/cm$^2$]) load. Note that AAP is referred to as Absorption Under Pressure in ERT 442.2-02, but it has substantially the same meaning as above. Additionally, in the present invention and Examples, the measurement was carried out by changing a loading condition to 4.83 kPa (0.7 psi, 49 [g/cm$^2$]).

(c) "Ext" (ERT 470.2-02)

"Ext" is an abbreviation for extractables, and means water soluble component (water soluble component amount) of a water absorbent resin. More specifically, the Ext is an amount of dissolved polymer (unit; wt %) measured by adding 1.0 g of the water absorbent resin into 200 ml of a 0.9 wt % aqueous sodium chloride solution with stirring for 16 hours at 500 rpm. The measurement of the amount of dissolved polymer is carried out by pH titration.

(d) "PSD" (ERT 420.2-02)

"PSD" is an abbreviation for Particle Size Distribution and means a particle size distribution measured by sieving classification. Additionally, a weight average particle diameter (D50) and a logarithmic standard deviation ($\sigma\zeta$) of particle diameter can be measured by the same method as in "(3) Mass-average particle diameter (D50) and logarithmic standard deviation ($\sigma\zeta$) of particle diameter distribution" described in EP 1594556 B1, p. 20, lines 11 to 30. Meanwhile, for measuring a particle diameter of the particulate water-containing gel-like crosslinked polymer, the measurement is carried out according to the method described in JP 2000-063527 A.

(e) "Liquid Permeability"

In the present invention, "liquid permeability" means a flow of a liquid flowing among particles of swollen gel under load or without load. The "liquid permeability" can be measured by a method for SFC (Saline Flow Conductivity) or GBP (Gel Bed Permeability) as a representative measurement method.

The "SFC (Saline Flow Conductivity)" is liquid permeability of a 0.69 wt % aqueous sodium chloride solution relative to 1.5 g of a water absorbent resin under load of 2.07 kPa (0.3 psi). It is measured according to an SFC testing method described in U.S. Pat. No. 5,669,894. The "GBP (Gel Bed Permeability)" is liquid permeability of a 0.69 wt % aqueous sodium chloride solution relative to a water absorbent resin under load or with free swell. It is measured according to a GBP testing method described in WO 2005/016393 A.

(f) "Moisture Content" (ERT 430.2-02)

"Moisture Content" means a water content of water absorbent resin. To be specific, the moisture content (unit; wt %) is calculated from drying loss obtained by drying 1 g of a water absorbent resin at 105° C. for 3 hours. Further, in the present invention, a drying temperature was changed to 180° C., the measurement was carried out 5 times for each sample, and an average value calculated from the five measurements was employed. Also, a value calculated by {100−water content (wt %)} is "resin solid content" in the present invention.

Hereinafter, in Examples 1 to 6 and Comparative Examples 1 to 7, effects of TS, TG, and TT were examined by carrying out polymerization of an aqueous monomer solution having TW of 40° C. or higher with reference to Patent Literatures 6 to 8 and Patent Literatures 36 to 41. As a polymerization method, a continuous kneader polymerization (stirring polymerization) as described in Patent Literatures 8 and 41 to 43 was used in Example 6 and Comparative Example 7, and a stationary polymerization (batch type model of continuous belt polymerization) as described in Patent Literatures 1 to 7 and Patent Literatures 36 to 40 was used in Examples 1 to 5 and Comparative Examples 1 to 6.

Example 1

Polymerization Solution Preparation Step

An aqueous monomer solution (1) was prepared by adding and mixing 421.7 g of acrylic acid, 2.75 g (molecular weight of 523) of polyethylene glycol diacrylate as an internal cross-linking agent, 11.60 g of 2 wt % aqueous solution of ethylene diamine tetramethylene phosphonic acid 5 sodium salt (EDTMP·5Na) as a chelating agent, 140.4 g of aqueous 48.5 wt % sodium hydroxide solution, and 394.2 g of deionized water (ion-exchanged water). In this case, a peak temperature of the aqueous monomer solution was 62° C.

After cooling the aqueous monomer solution (1), 211.9 g of 48.5 wt % sodium hydroxide aqueous solution which temperature was controlled to 40° C. was added thereto and mixed therein, to obtain an aqueous monomer solution (2). In this case, a temperature of the aqueous monomer solution (2) was increased to 78° C. with neutralization heat of a second step.

(Polymerization Step)

Immediately after 17.55 g of aqueous 4 wt % sodium persulfate solution was added to the aqueous monomer solution (2) with stirring, the solution was poured into a polymerization chamber (bottom of 300×300 mm, dam height of 22 mm, bottom material: Teflon (registered trademark) (thickness of 0.5 mm)). Further, a temperature (TW) of the aqueous monomer solution (2) added with a polymerization initiator was 78° C. Furthermore, a water content (PW) of the aqueous monomer solution (2) was 57 wt %.

A ratio of an amount of the aqueous monomer solution to be supplied to a contact area of the polymerization chamber (a weight of the aqueous monomer solution (2) per unit area of a liquid contact part) was 13.3 kg/m² in this case. By providing the polymerization chamber on an aluminum plate (thickness of 1 mm) which temperature was controlled with circulating water of 60° C., TS was controlled to 60° C. By providing a wall around the polymerization chamber and blowing hot air (heated air) with a hot air generator, an ambient temperature (temperature of hot air (TG)=60° C.) was controlled to 60° C. At the temperature (60° C.) of the gas (hot air) supplied from the outside to the polymerization part, relative humidity was as listed in Table 1 below. Herein, TT is calculated to be (60° C.+60° C.)/2=60° C. Further, a temperature (TW) of the aqueous monomer solution over a period from the preparation of the aqueous solution to the start of polymerization was in the range of 70 to 78° C.

The aqueous monomer solution (TW=78° C.) begun to be turbid 52 seconds after an aqueous sodium persulfate solution was added, and then swelled and foamed above the polymerization chamber in all directions while generating steam, to proceed polymerization (peak temperature of 112° C. in 70 seconds). Then, it was contracted to a size slightly bigger than the polymerization chamber. Herein, a water content (AW) of a water-containing gel-like crosslinked polymer (1) obtained at the time when the polymerization step was completed (3 minutes) was 47 wt %, and thus, a difference (PW−AW) between the water content (PW=57 wt %) of the aqueous monomer solution (2) and the water content (AW=47 wt %) of a polymerization product obtained at the time when the polymerization step was completed was 10 wt %.

(Gel Crushing Step)

The water-containing gel-like crosslinked polymer (1) (hydrogel) obtained from the polymerization was equally cut into 16 pieces and crushed with a meat chopper (produced by Iizuka Kogyo Co., Ltd., MEAT-CHOPPER TYPE: 12VR-400KSOX, die pore diameter: 9.5 mm), to obtain crushed hydrogel (1). In this case, an amount of the hydrogel added was 420 g/min, and along with addition of the hydrogel, deionized water which temperature was controlled to 90° C. was added in a rate of 50 g/min.

(Drying·Pulverizing·Classification Steps)

The crushed hydrogel (1) was dried with hot air at 180° C. for 40 minutes. The resultant dried product was pulverized with a roll mill (produced by Inoguchi Giken, Ltd., WML type roll pulverizer), and then classified with a JIS standard sieve with a mesh size of 710 μm. Particles passing through the sieve with a mesh size of 710 μm were classified with a JIS standard sieve with a mesh size of 150 μm, to remove water absorbent resin particles passing through the sieve with a mesh size of 150 μm, and to obtain a water absorbent resin (a). In this case, an amount of fine powder (particles of 150 μm or less) generated in this step was 20 wt % relative to the total weight of the pulverized product, and this amount was defined as a generation amount of fine powders (wt %).

(Fine Powder-Agglomerating Step)

The fine powders removed during the previous pulverizing·classification steps were agglomerated according to the method of Granulation Example 1 as described in Patent Literature 29 (U.S. Pat. No. 6,228,930 A). The agglomerated fine powders were pulverized and classified in the same manner as in the previous (drying·pulverizing·classification) steps, to obtain agglomerated water absorbent resin (b).

(Mixing Step of Agglomerated Fine Powder)

A water absorbent resin powder was obtained by mixing the water absorbent resin (a) in an amount of 80 wt % with the water absorbent resin (b) in an amount of 20 wt %, so as that a ratio of the water absorbent resin (b) to a mixture of the water absorbent resin (a) and water absorbent resin (b) was the same as a ratio of a generation amount of the fine powders. The resultant water absorbent resin powder had a weight average particle diameter (D50) of 431 μm and a logarithmic standard deviation (σ) of particle size distribution of 0.36.

(Surface Cross-Linking Step)

A surface cross-linking agent solution containing 0.4 parts by weight of ethylene carbonate, 0.6 parts by weight of propylene glycol, and 3.1 parts by weight of deionized water was uniformly sprayed to and mixed with 100 parts by weight of the resultant water absorbent resin particles. The water absorbent resin particles mixed with the surface cross-linking agent were heated for a certain time with a heater including a jacket equipped with a stirring blade (jacket temperature: 210° C.) so as yield CRC of 27 g/g (ERT 441.2-02). After heating, the resultant water absorbent resin was allowed to pass through a JIS standard sieve with a mesh size of 850 μm, to obtain a surface cross-linked water absorbent resin.

A mixture containing 0.8 parts by weight of a aqueous 27 wt % (8 wt % in terms of aluminum oxide) aluminum sulfate solution, 0.134 parts by weight a 60 wt % sodium lactate aqueous solution, and 0.016 parts by weight of propylene glycol was added to 100 parts by weight of the resultant surface cross-linked water absorbent resin. After addition, the water absorbent resin was dried with no wind at 60° C. for 30 minutes. The water absorbent resin was allowed to pass through a JIS standard sieve with a mesh size of 850 μm, to obtain a water absorbent resin (1).

Data during polymerization of the present Example, physical properties of the resultant water absorbent resin (1), and an amount of fine powders generated (=amount of fine powders recycled) were as listed in Table 1.

Example 2

In the present Example 2, a water absorbent resin (2) was obtained by polymerizing·drying·pulverizing, recycling and mixing of the whole fine powders passing through a sieve with a mesh size of 150 μm, and surface cross-linking in the same manner as in Example 1 except that a temperature (corresponding to TS) of floor circulating water was changed to 40° C. during polymerization. Data during polymerization of the present Example, physical properties of the resultant water absorbent resin (2), and an amount of fine powders generated (=amount of fine powders recycled) were as listed in Table 1.

Example 3

In the present Example 3, a water absorbent resin (3) was obtained in the same manner as in Examples 1 and 2 except that a temperature (corresponding to TS) of floor circulating water was changed to 80° C. during polymerization. Data during polymerization of the present Example, physical properties of the resultant water absorbent resin (3), and an amount of fine powders generated (=amount of fine powders recycled) were as listed in Table 1.

Example 4

In the present Example 4, a water absorbent resin (4) was obtained in the same manner as in Example 1 except that a temperature (TG) of a gas part was changed to 40° C. during polymerization. Data during polymerization of the present Example, physical properties of the resultant water absorbent resin (4), and an amount of fine powders generated (=amount of fine powders recycled) were as listed in Table 1.

Example 5

In the present Example 5, a water absorbent resin (5) was obtained in the same manner as in Example 1 except that a temperature (TG) of a gas part was changed to 80° C. during polymerization. Data during polymerization of the present Example, physical properties of the resultant water absorbent resin (5), and an amount of fine powders generated (=amount of fine powders recycled) were as listed in Table 1.

Example 6

A continuous kneader polymerization (stirring polymerization) was performed as disclosed in Patent Literatures 8 and 41 to 43, except using TW, TS, TG, and TT as follows.

An aqueous monomer solution prepared by line-mixing of 467.4 g of acrylic acid, 3.05 g (molecular weight of 523) of polyethylene glycol diacrylate as an internal cross-linking agent, 12.9 g of aqueous 2 wt % ethylene diamine tetramethylene phosphonic acid 5 sodium salt (EDTMP·5Na) solution as a chelating agent, 390.5 g of aqueous 48.5 wt % sodium hydroxide solution, 436.9 g of deionized water, and 19.45 g of 4 wt % sodium sulfate aqueous solution per minute was continuously supplied to a continuous kneader (produced by Dalton Co., Ltd., CKDJS-40) as a polymerization chamber including biaxial stirring blades. In this case, a ratio of an amount of the aqueous monomer solution supplied to a contact area of the polymerization chamber (a weight of the aqueous monomer solution per unit area of a liquid contact part) was 20.0 kg/m$^2$.

Further, a temperature of the aqueous monomer solution at the time when the aqueous monomer solution was supplied into the polymerization chamber was 78° C., a temperature of a jacket (corresponding to TS) of the polymerization chamber was adjusted to 50° C., and a temperature of a gas part (corresponding to TG) was adjusted to 80° C. by introducing heated nitrogen into the polymerization chamber.

The aqueous monomer solution became turbid 59 seconds after the aqueous monomer solution was supplied into the polymerization chamber. After a water-containing gel-like crosslinked polymer was crushed during polymerization, the crushed hydrogel was continuously discharged from the polymerization chamber about 10 minutes after the supply of the aqueous monomer solution. Further, a peak temperature during polymerization was about 102° C.

A water absorbent resin (6) was obtained by drying, pulverizing, recycling and mixing of the whole fine powders passing through a sieve with a mesh size of 150 μm, and surface cross-linking in the same manner as in Example 1 in the steps after the polymerization step and the gel agglomeration step. Data during polymerization of the present Example, physical properties of the resultant water absorbent resin (6), and an amount of fine powders generated (=amount of fine powders recycled) were as listed in Table 1.

Comparative Example 1

In the present Comparative Example 1, a comparative water absorbent resin (1) was obtained in the same manner as in Example 1 except that a temperature (corresponding to TS) of floor circulating water was changed to 30° C. during polymerization. Herein, TT was 45° C. Data during polymerization of the present Example, physical properties of the resultant comparative water absorbent resin (1), and an amount of fine powders generated (=amount of fine powders recycled) were as listed in Table 1.

Comparative Example 2

In the present Comparative Example 2, a comparative water absorbent resin (2) was obtained in the same manner as in Example 1 except that a temperature (corresponding to TS) of floor circulating water was changed to 90° C. during polymerization. Herein, TT was 75° C. Data during polymerization of the present Example, physical properties of the resultant comparative water absorbent resin (2), and an amount of fine powders generated (=amount of fine powders recycled) were as listed in Table 1.

Comparative Example 3

In the present Comparative Example 3, a comparative water absorbent resin (3) was obtained in the same manner as in Example 1 except that a temperature (corresponding to TG) of a gas part was changed to 30° C. during polymerization. Herein, TT was 45° C. Data during polymerization of the present Example, physical properties of the resultant comparative water absorbent resin (3), and an amount of fine powders generated (=amount of fine powders recycled) were as listed in Table 1.

Comparative Example 4

In the present Comparative Example 4, a comparative water absorbent resin (4) was obtained in the same manner as in Example 1 except that a temperature (corresponding to TG) of a gas part was changed to 100° C. during polymerization. Herein, TT was 80° C. Data during polymerization of the present Example, physical properties of the resultant comparative water absorbent resin (4), and an amount of fine powders generated (=amount of fine powders recycled) were as listed in Table 1.

Comparative Example 5

In the present Comparative Example 5, a comparative water absorbent resin (5) was obtained in the same manner as in Example 5 except that a temperature (corresponding to TS) of floor circulating water was changed to 90° C. during polymerization. Herein, TT was 85° C. Data during polymerization of the present Example, physical properties of the resultant comparative water absorbent resin (5), and an amount of fine powders generated (=amount of fine powders recycled) were as listed in Table 1.

Comparative Example 6

In the present Comparative Example 6, a comparative water absorbent resin (6) was obtained in the same manner as in Example 6 except that a jacket temperature (corresponding to TS) of the polymerization chamber was changed to 100° C. Herein, TT was 90° C. Data during polymerization of the present Example, physical properties of the resultant comparative water absorbent resin (6), and an amount of fine powders generated (=amount of fine powders recycled) were as listed in Table 1.

Comparative Example 7

In the present Comparative Example 7, a comparative water absorbent resin (7) was obtained in the same manner as in Example 6 except that a temperature (corresponding to TG) of a gas part was changed to 20° C. during a continuous kneader polymerization. Herein, TT was 35° C. Data during polymerization of the present Example, physical properties of the resultant comparative water absorbent resin (7), and an amount of fine powders generated (=amount of fine powders recycled) were as listed in Table 1.

TABLE 1

|  | Contact part temperature (TS) (° C.) | Gas part temperature (TG) (° C.) | Induction time* (sec) | Generation amount of fine powder (wt %) | SFC | TT | Relative humidity (%) |
|---|---|---|---|---|---|---|---|
| Example 1 | 60 | 60 | 52 | 20 | 100 | 60 | 10 or lower |
| Example 2 | 40 | 60 | 61 | 21 | 94 | 50 | 10 or lower |
| Example 3 | 80 | 60 | 39 | 24 | 97 | 70 | 10 or lower |
| Example 4 | 60 | 40 | 60 | 20 | 95 | 50 | 25 to 30 |
| Example 5 | 60 | 80 | 48 | 23 | 98 | 70 | 10 or lower |
| Example 6 | 50 | 80 | 59 | 22 | 97 | 65 | 10 or lower |
| Comparative Example 1 | 30 | 60 | 68 | 18 | 86 | 45 | 10 or lower |
| Comparative Example 2 | 90 | 60 | 33 | 27 | 90 | 75 | 10 or lower |
| Comparative Example 3 | 60 | 30 | 67 | 19 | 87 | 45 | 45 to 50 |
| Comparative Example 4 | 60 | 100 | 44 | 26 | 89 | 80 | 10 or lower |
| Comparative Example 5 | 90 | 80 | 29 | 28 | 90 | 85 | 10 or lower |
| Comparative Example 6 | 100 | 80 | 20 | 30 | 88 | 90 | 10 or lower |
| Comparative Example 7 | 50 | 20 | 79 | 18 | 84 | 35 | 80 to 85 |

*Induction time: Time from when an initiator is supplied until when a monomer solution is turbid.

Table 1 illustrates a temperature (TS) of a liquid contact part, a temperature (TG) of a gas part (gas), an induction time, a generation amount of fine powders, and SFC. A value of SFC is obtained by using a water absorbent resin having CRC adjusted to be 27 through surface cross-linking. Further, although not listed in Table 1, in Examples 1 to 6 and Comparative Examples 1 to 6, polymerization time except kneader polymerization was set to 3 minutes, and a peak temperature was set in the range of 110 to 114° C., and a peak time was about 60 seconds (50 to 75 seconds).

FIG. 1 is a graph illustrating TS and TG in Examples and Comparative Examples.

Figure 2:
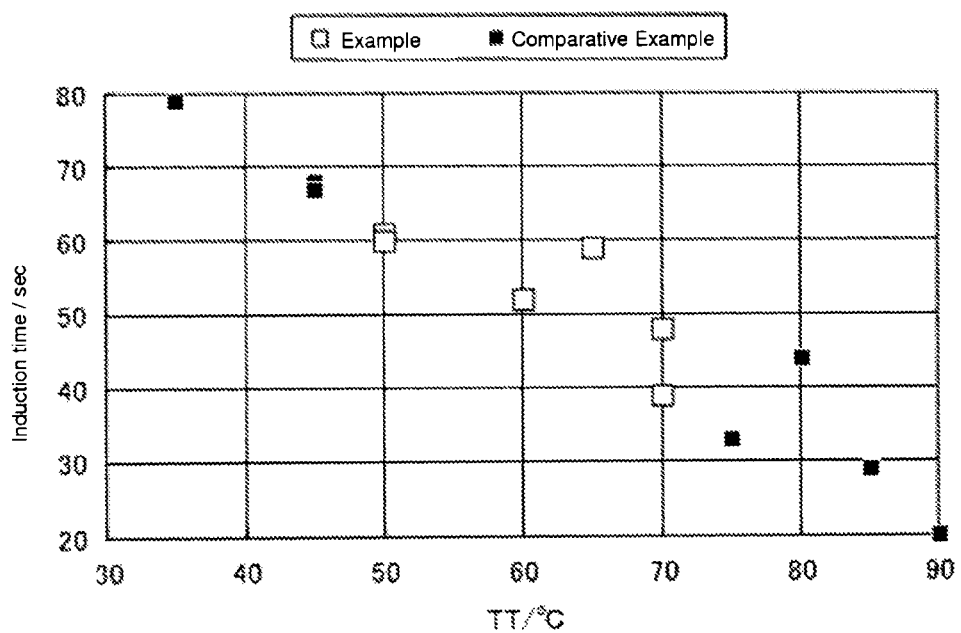
FIG. 2 is a graph illustrating the relationship between TT (° C.) and an induction time (sec) in the Examples and Comparative Examples.

FIG. 2 is a graph illustrating a relationship between TT (° C.) and an induction time (sec) in Examples and Comparative Examples. It can be seen that even with the same temperature (TW) of the aqueous monomer solution, when TT is 45° C. or lower, an induction time is lengthened and productivity is decreased. Further, it can be seen that when TT is 75° C. or higher, an induction time is too much shortened and the aqueous monomer solution may be polymerized before it is diffused to a polymerization chamber (for example, a belt) within the polymerization part. That is, it can be seen that polymerization stability can be improved by controlling a temperature.

Figure 3:
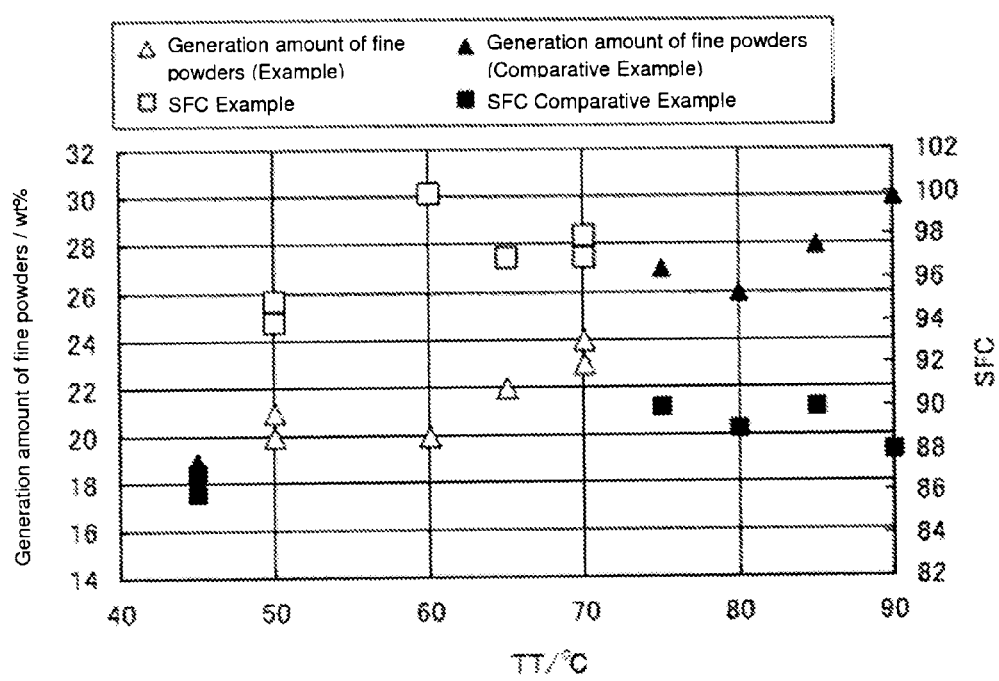
FIG. 3 is a graph illustrating the relationship among TT (° C., horizontal axis), a generation amount of fine powders (wt %, vertical axis on the left), and SFC (vertical axis on the right) in the Examples and Comparative Examples.

FIG. 3 is a graph illustrating a relationship among TT (° C., horizontal axis), a generation amount of fine powders (wt %, vertical axis on the left), and SFC (vertical axis on the right) in Examples and Comparative Examples. FIG. 3 demonstrates that as TT is increased, a generation amount of fine powders is increased and SFC is decreased, while when the TT is decreased to 45° C., a generation amount of fine powders is decreased and the SFC is also decreased. Thus, it can be seen that in Examples, by setting the TT in the range of 47 to 73° C., the generation amount of fine powders (Δ) is small and the SFC (□) is high.

Comparative Example 8

From the foregoing, it can be seen that it is important to control a temperature (TS) of a polymerization apparatus in contact with an aqueous monomer solution, a temperature (TG) of a gas part, and TT. Now, effects of a temperature (TS) of the polymerization apparatus in contact with polymerized gel during polymerization, but not in contact with the aqueous monomer solution, and a temperature (TG) of a gas part, and TT were examined.

By comparison between Example 1 (TG=60° C.) and Comparative Example 3 (TG=30° C.), it can be seen that the temperature (TG) of the gas part in contact with the aqueous monomer solution is important for SFC or an amount of fine powders. Comparative Example 8 was carried out in the same manner as in Comparative Example 3 except that a temperature of a gas was changed to 60° C. after a polymerization was started at TG of 30° C. in Comparative Example 3. An amount of fine powders and SFC of the resultant water absorbent resin (8) were equivalent to those of Comparative Example 3, and it can be seen that it is not important to control a temperature of the gas part in contact with the polymerized gel in the range of 40 to 90° C.

Comparative Example 9

By comparison between Example 6 (TS=50° C.) and Comparative Example 6 (TS=100° C.), it can be seen that the temperature (TS) of the polymerization apparatus in contact with the aqueous monomer solution is important for SFC or an amount of fine powders. Comparative Example 9 was carried out in the same manner as in Comparative Example 6 except that after a polymerization was started in the polymerization chamber having TS of 100° C. in Comparative Example 6, polymerized gel was transferred to another polymerization chamber having TS of 60° C. An amount of fine powders and SFC of the resultant water absorbent resin (9) were equivalent to those of Comparative Example 3, and it can be seen that it is not important to control a temperature of the polymerization apparatus in contact with the polymerized gel in the range of 35 to 85° C.

Comparative Example 10

A water-containing gel-like crosslinked polymer was obtained by performing a continuous belt polymerization (TW=93° C., TS=70° C.) according to Example 2 of Patent Literature 40 (US 2011/0021725). Patent Literature 40 discloses a continuous polymerization having PW of 57%, TW of 93° C., and TS of 60 to 70° C. as defined in the present disclosure. However, it does not disclose a temperature (corresponding to TG of the present disclosure) of a gas part of a belt polymerization apparatus, and it was measured to be found to be 20° C. Herein, since TS is 70° C., TT is calculated to be 45° C. in the Example 2. It can be seen that Patent Literature 40 does not disclose TG and does not satisfy TG as defined in the present disclosure.

With respect to the water-containing gel-like crosslinked polymer obtained according to Example 2 of Patent Literature 40, the steps (drying·pulverizing·classification· and surface cross-linking) after the gel crushing step were performed in the same manner as Example 1 of the present disclosure, to obtain a comparative water absorbent resin (10). SFC at CRC of 27 g/g was 89.

Example 7

In the present Example 7, a water absorbent resin (7) was obtained in the same manner as in Comparative Example 10 except that a temperature (corresponding to TG) of a gas part was adjusted to 50° C. during polymerization in Comparative Example 10 by introducing warm air (5 m³/min) from a side of the monomer supply unit of the continuous belt polymerization apparatus so as to yield TT of 60° C. SFC at CRC of 27 g/g was 97. By comparison between Example 7 and Comparative Example 10, it can be seen that an absorption property (SFC) can be improved through a continuous belt polymerization by controlling TG in the range of 40 to 90° C.

Comparative Example 11

A continuous polymerization was carried out according to Example 1 of Patent Literature 36 (U.S. Pat. No. 7,622,535 A). That is, by using the continuous belt polymerization apparatus as illustrated in FIG. 1 of Patent Literature 36, an aqueous sodium acrylate solution having a concentration of 45% (PW of 55% in the present disclosure) and a neutralization rate of 70% was polymerized at a temperature of 98° C. (corresponding to TW in the present disclosure) by an endless belt polymerization apparatus having a temperature of 100° C. (TS in the present disclosure) and then dried and pulverized, to obtain a comparative water absorbent resin (11).

Patent Literature 36 discloses continuous polymerization having PW of 55%, TW of 98° C., and TS of 100° C. as defined in the present disclosure. However, it does not disclose a temperature (TG in the present disclosure) of a gas part (around and near an inlet opening 110 of a monomer inlet opening as illustrated in FIG. 1), and it was measured to be found to be 18 to 22° C. It can be seen that Patent Literature 36 does not disclose TG and does not satisfy TG (40 to 90° C.) as defined in the present disclosure.

Comparative Example 12

A continuous polymerization was carried out according to Example 1 of Patent Literature 37 (US 2006/0167198 A). That is, by using the continuous belt polymerization apparatus as illustrated in FIGS. 1 to 4 of Patent Literature 37, an aqueous sodium acrylate solution having a concentration of 46% (PW of 54% in the present disclosure) and a neutralization rate of 70% was polymerized at a temperature of 98° C. (corresponding to TW in the present disclosure) by an endless belt polymerization apparatus having a temperature of 100° C. (TS in the present disclosure) and then dried and pulverized, to obtain a comparative water absorbent resin (11).

Patent Literature 37 discloses continuous polymerization having PW of 54%, TW of 98° C., and TS of 100° C. as defined in the present disclosure. However, it does not disclose a temperature (TG in the present disclosure) of a gas part, and it was measured to be found to be about 17 to 21° C. It can be seen that Patent Literature 36 does not disclose TG and does not satisfy TG (40 to 90° C.) as defined in the present disclosure.

Comparative Example 13

Continuous polymerization was carried out according to Example 1 of Patent Literature 38 (U.S. Pat. No. 7,694,900 A). That is, by using the continuous belt polymerization apparatus as illustrated in FIG. 1 of Patent Literature 38, an aqueous sodium acrylate solution having a concentration of 53% (PW of 47% in the present disclosure) and a neutralization rate of 70% was polymerized at a temperature of 95° C. (corresponding to TW in the present disclosure) by an endless belt polymerization apparatus having a temperature of 100° C. (TS in the present disclosure) and then dried and pulverzied, to obtain a comparative water absorbent resin (12).

Patent Literature 38 discloses continuous polymerization having PW of 47%, TW of 95° C., and TS of 100° C. as defined in the present disclosure. However, it does not disclose a temperature (TG in the present disclosure) of a gas part, and it was measured to be found to be about 18 to 22° C. It can be seen that Patent Literature 36 does not disclose TG and does not satisfy TG (40 to 90° C.) as defined in the present disclosure.

Comparative Example 14

Continuous polymerization was carried out according to Example 1 of Patent Literature 39 (U.S. Pat. No. 7,638,078 A). That is, by using the continuous belt polymerization apparatus, an aqueous sodium acrylate solution having a concentration of 45% (PW of 55% in the present disclosure) and a neutralization rate of 70% was polymerized at a temperature of 95° C. (corresponding to TW in the present disclosure) by an endless belt polymerization apparatus having a temperature of 100° C. (TS in the present disclosure) and then dried and pulverized, to obtain a comparative water absorbent resin (13).

Patent Literature 39 discloses continuous polymerization having PW of 55%, TW of 95° C., and TS of 100° C. as defined in the present disclosure. However, it does not disclose a temperature (TG in the present disclosure) of a gas part, but it was measured to be found to be about 18 to 22° C. It can be seen that Patent Literature 36 does not only disclose TG and does not satisfy TG (40 to 90° C.) as defined in the present disclosure.

SUMMARY

As listed in Table 1 and FIG. 3, it can be seen that according to the production method of the present invention, by controlling three temperatures, that is, temperatures of a contact part (TS) and a gas (TW), at immediately early polymerization stage, and an average value (TT) thereof, a generation amount of fine powders passing through a sieve with a mesh size of 150 μm can be decreased to improve SFC.

Patent Literatures 6 to 8 and Patent Literatures 36 to 45 disclose TS or TW but do not disclose TG (typically, when a temperature of a gas is not described, it can be construed as room temperature). In Examples of Patent Literatures 6 to 8 and Patent Literatures 36 to 40, it is disclosed that a belt temperature or a hot plate temperature is 100° C. (corresponding to TS in the present disclosure). However, Patent Literatures 6 to 8 and Patent Literatures 36 to 43 do not suggest a polymerization with a combination of TG (40 to 90° C.) in a specific range, TS (35 to 85° C.) and TT (47 to 73° C.) in a specific range and do not disclose that through polymerization with controlled TG/TS/TW and more preferably with controlled TW (40° C. to lower than 100° C.), an amount of fine powders can be reduced after drying and physical properties (particularly, liquid permeability (SFC)) can be improved.

In the present invention, regarding liquid permeability that has been conventionally made sacrifice of water absorption capacity, the water absorbent resin can satisfy both high water absorption capacity of CRC≥25 and high liquid permeability of SFC≥90 (preferably, SFC≥94, and more preferably, SFC≥96). In particular, the present invention can reduce a generation amount of fine powders so as to stabilize polymerization and to improve physical properties (particularly, liquid permeability (SFC)) by combination with a technique (Patent Literatures 6 to 8 and Patent Literatures 36 to 41) of polymerization in a boiling state (peak temperature of higher than 100° C.) or a polymerization at a high temperature (higher than 40° C.).

As clear from comparison with Example 1 (SFC=100, a generation amount of fine powders of 20%), even when a temperature (TG) of a gas part is 60° C., if a temperature (TS) of a contact part in Comparative Example 1 is as low as 30° C., SFC is greatly decreased to 86, and if a temperature (TS) of a contact part in Comparative Example 2 is as high as 90° C., SFC is greatly decreased to 90 and a generation amount of fine powders is greatly increased to 27%.

As clear from comparison with Example 1 (SFC=100, a generation amount of fine powders of 20%), even when a temperature (TS) of a contact part is 60° C., if a temperature (TG) of a gas part in Comparative Example 3 is as low as 30° C., SFC is greatly decreased to 87, and if a temperature (TS) of a contact part in Comparative Example 4 is as high as 100° C., SFC is greatly decreased to 89 and a generation amount of fine powders is greatly increased to 26%.

In conventional polymerization for a water absorbent resin as described in Patent Literatures 1 to 8 and Patent Literatures 36 to 45, such a temperature control is not disclosed. Further, conventionally, in order to reduce an amount of fine powders, classification methods of Patent Literatures 30 to 35 or various conventional recycling methods of Patent Literatures 25 to 29 have been suggested. Furthermore, in order to improve physical properties (particularly, to improve liquid permeability) of a water absorbent resin, various methods of Patent Literatures 1 to 24 have been suggested. In these circumstance, as a result of close study to solve the problems, that is reduction in fine powder and improvement in liquid permeability, the present inventors have found that it is important to correlatively control temperatures at immediately early polymerization stage, that is "a temperature (TS) of a chamber" and "a temperature (TG) of a gas part (gas)" in contact with a polymerization aqueous solution during polymerization rather than to individually control them, which has not been conceived to solve the above-described problems.

INDUSTRIAL APPLICABILITY

According to a method for producing a water absorbent resin of the present invention, by controlling temperatures of a chamber and a gas in contact with a reaction solution during polymerization, it is possible to obtain a water absorbent resin with less fine powders (passing through a sieve with a mesh size of 150 μm) and excellent physical properties, particularly high liquid permeability (for example, high SFC).

The present application is based on Japanese Patent Application No. 2011-251103 filed on Nov. 16, 2011, and the disclosure is incorporated herein by reference in its entirety.

The invention claimed is:

1. A method for producing a polyacrylic acid (salt)-based water absorbent resin, the method comprising a polymerization step of supplying as a base material an aqueous solution containing an acrylic acid and/or an acrylic acid salt as a monomer component and polymerizing the monomer in the presence of a polymerization initiator, wherein in the polymerization step, there is used a polymerization apparatus which comprises a polymerization part covered with a case, said polymerization part comprising at least a supply line for supplying the aqueous solution, an external gas supply port, and a gas discharge port, and has a structure that a liquid contact part in contact with the aqueous solution and a gas supplied from the outside of the polymerization apparatus are brought into contact with the aqueous solution during a polymerization, and wherein a controlled temperature of the liquid contact part is set as TS, a temperature of the gas is set as TG, and TT is (TS+TG)/2, the polymerization is carried out under temperature conditions satisfying the following Equations 1 to 3

$$35° C. \leq TS \leq 85° C. \quad \text{Equation 1}$$

$$40° C. \leq TG \leq 90° C. \quad \text{Equation 2}$$

$$47° C. \leq TT \leq 73° C. \quad \text{Equation 3}$$

2. The method according to claim 1, wherein in the polymerization step, the temperature, TW, of the aqueous solution to be supplied to the polymerization part is not less than 40° C. and lower than 100° C.

3. The method according to claim 2, wherein in the polymerization step, the temperature, TW, of the aqueous solution is not lower than 40° C. over a period from the preparation of the aqueous solution to the start of polymerization.

4. The method according to claim 1, wherein a weight of the aqueous solution per unit area at a site of the polymerization part in contact with the aqueous solution is 6.2 to 23.4 kg/m$^2$.

5. The method according to claim 1, wherein a water content, PW, of the aqueous solution is 70 wt % or less.

6. The method according to claim 5, wherein a difference (PW−AW) between the PW and the AW is 5 wt % or more, wherein "AW" is a water content of a polymerization product obtained at the time when the polymerization step is completed.

7. The method according to claim 1, wherein the polymerization apparatus is a continuous kneader type apparatus or a continuous belt type apparatus.

8. The method according to claim 1, the method further comprising a drying step, a pulverization step; and a surface cross-linking step.

9. The method according to claim 1, the method further comprising a fine powder recycling step.

10. The method according to claim 1, wherein a polymerization peak temperature is higher than 100° C.

11. The method according to claim 1, wherein a polymerization time is 10 minutes or shorter.

12. The method according to claim 1, wherein the gas contains oxygen.

13. The method according to claim 1, wherein the gas contains air as a main component of the gas.

14. The method according to claim 1, wherein a temperature of the gas supplied from the outside is 40 to 90° C.

15. The method according to claim 1, wherein supply of the gas from the outside is carried out by gas supply and/or suction.

16. The method according to claim 1, wherein an amount (m$^3$/min) of the gas supplied is in the range of 0.01 to 1000 m$^3$/min.

17. The method according to claim 1, wherein the polymerization initiator is a heat decomposition type polymerization initiator.

* * * * *